US012702511B1

(12) United States Patent
Wang et al.

(10) Patent No.: US 12,702,511 B1
(45) Date of Patent: Aug. 11, 2026

(54) SYSTEMS AND METHODS FOR REMOTELY CONTROLLING ROBOTIC-ASSISTED MEDICAL PROCEDURES

(71) Applicant: Sovato Health, Inc., Goleta, CA (US)

(72) Inventors: Yulun Wang, Santa Barbara, CA (US); Blair Whitney, Santa Barbara, CA (US)

(73) Assignee: Sovato Health, Inc., Goleta, CA (US)

( * ) Notice: Subject to any disclaimer, the term of this patent is extended or adjusted under 35 U.S.C. 154(b) by 0 days.

(21) Appl. No.: 19/420,171

(22) Filed: Dec. 15, 2025

(51) Int. Cl.
*A61B 34/37* (2016.01)
*A61B 34/00* (2016.01)
*A61B 34/30* (2016.01)

(52) U.S. Cl.
CPC ............. *A61B 34/37* (2016.02); *A61B 34/25* (2016.02); *A61B 2034/301* (2016.02)

(58) Field of Classification Search
CPC ... A61B 34/37; A61B 34/25; A61B 2034/301; A61B 34/35; A61B 90/36; G16H 40/40
See application file for complete search history.

(56) References Cited

U.S. PATENT DOCUMENTS 7,222,000 B2 5/2007 Wang et al.
7,289,883 B2 10/2007 Wang et al.
7,292,912 B2 11/2007 Wang et al.
7,761,185 B2 7/2010 Wang et al.
8,209,051 B2 6/2012 Wang et al.
8,340,819 B2 12/2012 Mangaser et al.
8,463,435 B2 6/2013 Herzog et al.
8,836,751 B2 9/2014 Ballantyne et al.
8,849,680 B2 9/2014 Wright et al.
9,138,891 B2 9/2015 Herzog et al.
9,160,783 B2 10/2015 Pinter
9,198,728 B2 12/2015 Wang et al.
9,251,313 B2 2/2016 Ross et al.
9,264,664 B2 2/2016 Pinter et al.
9,375,843 B2 6/2016 Wang et al.
9,842,192 B2 12/2017 Wang et al.
9,849,593 B2 12/2017 Wang et al.
10,924,708 B2 2/2021 Pinter et al.
11,154,981 B2 10/2021 Hanrahan et al.
11,315,681 B2 4/2022 Armstrong et al.
11,633,533 B2 4/2023 Gregory et al.
11,636,944 B2 4/2023 Hanrahan et al.
12,042,239 B1 7/2024 Whitney et al.
(Continued)

OTHER PUBLICATIONS

Ghodoussi et al., "Robotic Surgery—The Transatlantic Case", Proceedings of the 2002 IEEE International Conference on Robotics & Automation, Washington, DC, May 2002, pp. 1882-1888.
(Continued)

*Primary Examiner* — Abby Lin
*Assistant Examiner* — Renee LaRose
(74) *Attorney, Agent, or Firm* — Knobbe, Martens, Olson & Bear, LLP

(57) ABSTRACT

Disclosed systems, apparatuses, and methods enable remotely controlling robotic-assisted medical systems, such as robotic-assisted surgery systems. Such disclosed approaches provide a scalable, flexible, and efficient system for access monitoring and managing robotic-assisted medical systems. Disclosed approaches improve efficiency, availability, and safety of robotic-assisted medical procedures.

21 Claims, 19 Drawing Sheets

(56) References Cited

U.S. PATENT DOCUMENTS

| | | | | |
|---|---|---|---|---|
| 12,089,906 | B1 | 9/2024 | Whitney et al. | |
| 2005/0204438 | A1 | 9/2005 | Wang et al. | |
| 2006/0047821 | A1 | 3/2006 | Kim | |
| 2008/0201017 | A1 | 8/2008 | Wang et al. | |
| 2011/0071702 | A1 | 3/2011 | Wang et al. | |
| 2018/0250086 | A1 | 9/2018 | Grubbs | |
| 2021/0220064 | A1 | 7/2021 | Kottenstette et al. | |
| 2023/0128665 | A1 | 4/2023 | Kottenstette et al. | |
| 2025/0339220 | A1* | 11/2025 | Brubaker | A61B 34/10 |

OTHER PUBLICATIONS

Gu et al., "Robotic surgery in China", The Innovation, Sep. 11, 2023, vol. 4, No. 5, in 2 pages.

Teladoc Health, Teladoc HealthTM Care Location App ModuleTM User Guide, 2021, in 71 pages.

Teladoc Health, "Teladoc HealthTM Lite V2 & V3 Under Guide", 2021, in 65 pages.

Edge Medical, Tele-Surgery System—Edge Medical World Leading and Fast-Growing Surgical Robot Company (2023), in 2 pages.

Crusco, et al., Comparing the da Vinci Si Single Console and Dual Console in Teaching Novice Surgeons Suturing Techniques, JSLS 18(3):1-6 (2014).

* cited by examiner

Figure 8B:
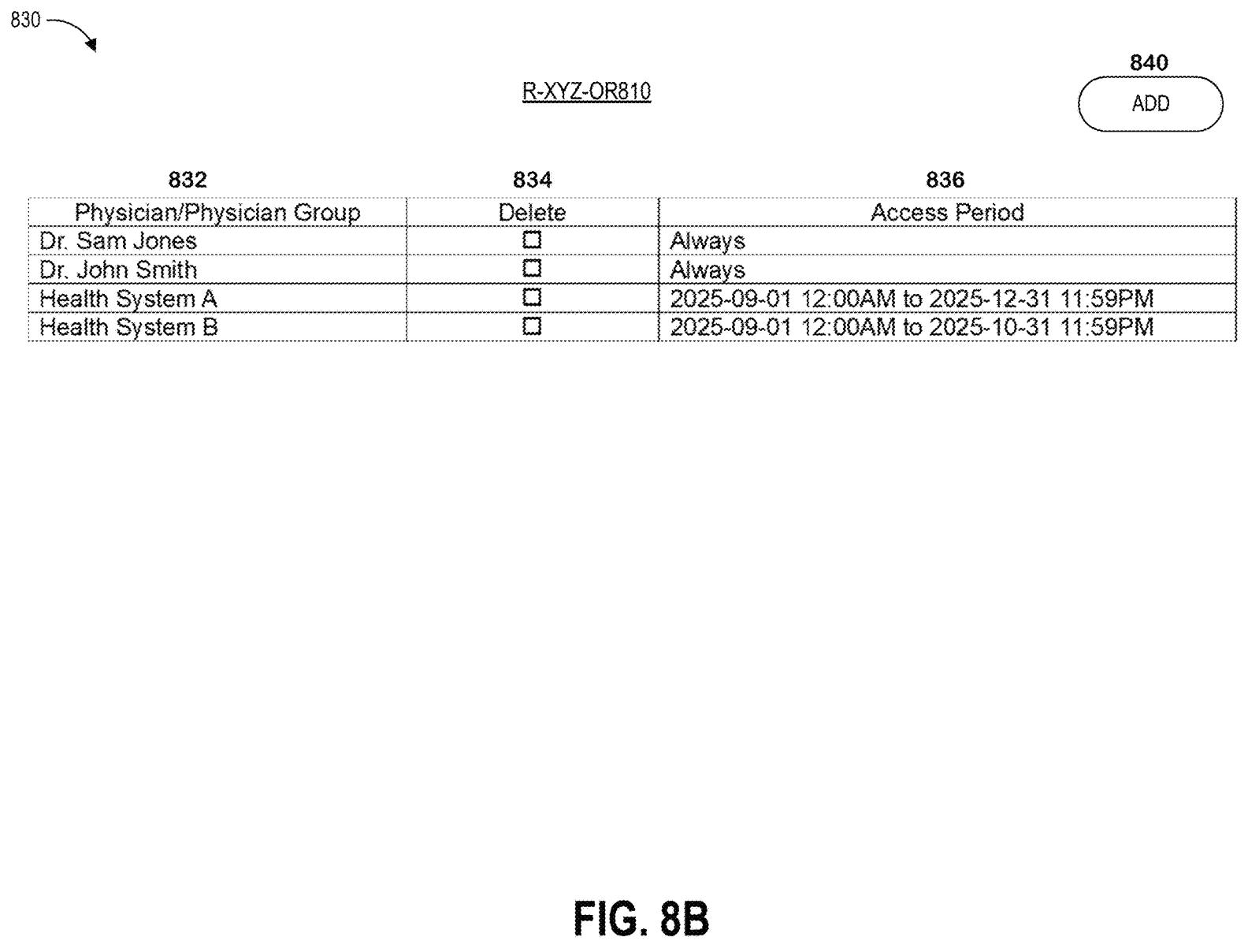

| Physician/Physician Group | Delete | Access Period |
|---|---|---|
| Dr. Sam Jones | ☐ | Always |
| Dr. John Smith | ☐ | Always |
| Health System A | ☐ | 2025-09-01 12:00AM to 2025-12-31 11:59PM |
| Health System B | ☐ | 2025-09-01 12:00AM to 2025-10-31 11:59PM |

R-XYZ-OR810

| Session ID | Time | Duration | Avg. Bandwidth | Packet Loss | Jitter | # Instrument Commands | Log |
|---|---|---|---|---|---|---|---|
| .... | .... | .... | .... | .... | .... | .... | .... |
| 1000 | | | | | | | Link |
| 1001 | | | | | | | Link |
| 1002 | | | | | | | Link |
| 1003 | | | | | | | Link |
| .... | .... | .... | .... | .... | .... | .... | .... |

Access Permissions: Robot R-ABC-OR003

Add Rule

| Group or User | Time Window | Actions |
|---|---|---|
| Randall Associates | Always | Modify Delete |

Access Permissions: Robot R-XYZ-OR810

Add Rule

994

| Group or User | Time Window | Actions |
|---|---|---|
| Springfield Surgical | Always | Modify Delete |
| Anne Archer | Nov 10, 6:00~17:00 | Modify Delete |

FIG. 10B

SYSTEMS AND METHODS FOR REMOTELY CONTROLLING ROBOTIC-ASSISTED MEDICAL PROCEDURES

TECHNICAL FIELD

This disclosure relates generally to approaches for remotely controlling robotic-assisted medical procedures, such as surgical procedures.

DESCRIPTION OF RELATED ART

Robot-assisted surgery systems are generally available and have been developed to operate efficiently and safely. A robotic surgery system typically includes robotically actuable surgical instruments that may be inserted within the patient's body to perform a surgical procedure at a physician site. The robotic surgery system is typically controlled by a physician via a physician input console, which is connected to the robotic surgery system via a control cable. The physician input console includes input devices that are grasped by the physician's hands and moved to generate signals for activating the surgical instruments to perform surgical operations at the surgical site. Signals are transmitted over the control cable to the robotic surgery system, which interprets the signals and generates control signals that cause the instruments to be actuated to perform surgical operations.

SUMMARY

For physicians or other medical professionals, advantageously, remote procedures facilitate optimal utilization of their time and provide access to a sufficient volume of patients to perfect their skills. For patients, advantageously, remote procedures create ample access to the right physician or medical professional and the right care at an affordable price, decreases the need for travel, and reduces delayed care. Approaches described herein can provide a secure network environment for health system administrators, robotic system manufacturers, and super users to access, manage, and manipulate various components of robotic-assisted medical systems that can be controlled remotely. Disclosed approaches facilitate patient safety and increase the effectiveness and availability of remotely controlled robotic procedures.

Disclosed systems, apparatuses, and methods enable remotely controlling robotic-assisted medical systems, such as robotic-assisted surgery systems, via an access monitoring management system (sometimes referred to as AAMS). Various different levels of user privileges can be utilized to allow different entities different levels of access to robotic-assisted medical systems that can be controlled remotely. Such disclosed approaches provide a scalable, flexible, and efficient hierarchy for controlling the operation of robotic-assisted medical systems that can be controlled remotely.

Other aspects and features will become apparent to those ordinarily skilled in the art upon review of the following description of specific disclosed implementations in conjunction with the accompanying figures.

BRIEF DESCRIPTION OF THE DRAWINGS

Specific implementations will now be described with reference to the following drawings, which are provided by way of example.

DETAILED DESCRIPTION

Figure 1:
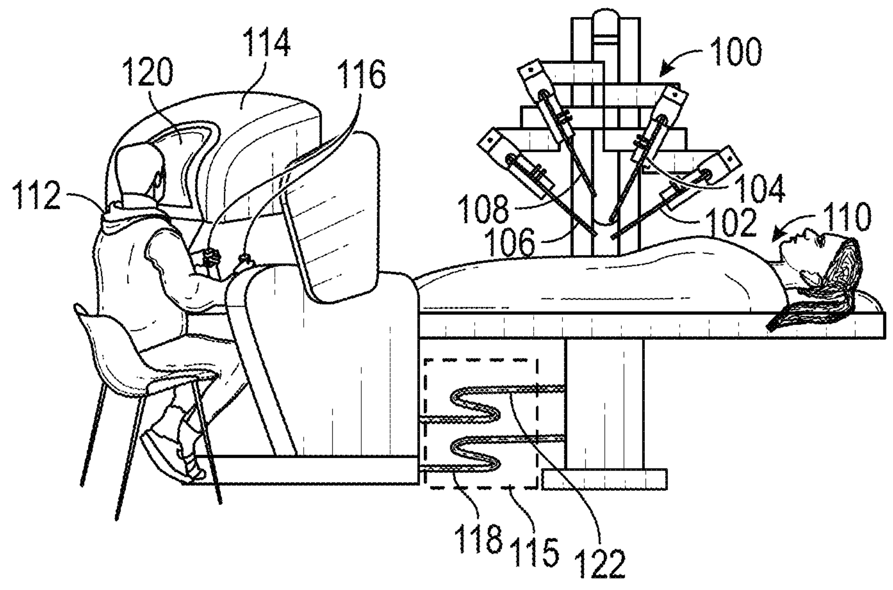
FIG. 1 is perspective view of a robotic surgery system.

Referring to FIG. 1, a robotic medical procedure system, in particular, a robotic surgery system is shown generally at 100. The robotic surgery system 100 includes a plurality of robotically actuable surgical instruments 102-108 positioned on one or more robotic arms. At least one of the instruments 102-108 will generally be configured as an in-patient imaging system (such as, a camera, fluoroscopy system which can obtain a continuous X-ray image, radiography system, computer tomography (CT) system, ultrasound system, magnetic resonance imaging (MRI) system, or the like), which may be inserted into the body of the patient to generate images of anatomical structures and the surgical instruments 102-108 at a surgical site within the body of a patient 110. In some instances, a plurality of imaging systems can be utilized by the robotic surgery system 100. In some cases, one or more imaging systems may not need to be inserted into the patient's body. The remaining instruments may be configured to include an end effector that performs a specific surgical function (such as, forceps/graspers, needle drivers, scissors, electrocautery hooks, staplers, clip appliers, removers, etc.). The system 100 is controlled by a surgeon 112 via a surgeon input console 114, which is connected to the robotic surgery system 100 via a control cable 118. The surgeon input console 114 includes input devices (not shown) including handles 116 that are grasped by the surgeon's left and right hands and moved within an input device workspace or otherwise actuated to generate input signals. The input devices include encoders that transform positions and orientations of the handles 116 into input signal data representing the surgeon input. The input signals may thus be used for activating the plurality of surgical instruments 102-108 to perform surgical operations at the surgical site. The input signals are transmitted over the control cable 118 to the system 100, which interprets the signals and generates control signals that cause the instruments 102-108 to be actuated to move and perform other surgical operations. The input signals will generally be output by the input devices on the surgeon input console 114 as data signals representing the inputs to the console provided by the surgeon 112. For example, the surgeon input console 114 may generate input signals in the form of motion control signals that represent instantaneous positions of the handles 116 of the input devices within an input device workspace. The data signals are transmitted over the control cable 118, which is generally a wired connection between the surgeon input console 114 and the robotic surgery system 100. The wired connection ensures negligible transmission delay such that operations of the surgical instruments 102-108 caused by the surgeon will be effected by the system 100 with negligible delay. Transmission over the control cable 118 may be implemented using any of a variety of different data transmission technologies such as Ethernet or Controller Area Network (CAN bus) protocol.

The robotic surgery system 100 can include a patient cart that supports the robotic arms. In some instances, a separate vision cart that supports one or more imaging systems can be included. The robotic surgery system 100 can also include a tower that serves as a central hub to which the patient cart and vision cart (if present) are connected. Any network connections to the robotic surgery system described herein can be made to the tower.

Additional input signals may also be generated at the surgeon input console 114. For example, the handles 116 may include other controls (not shown) that may be used to generate actuation signals that actuate operations at the surgical instruments 102-108, such as opening or closing a surgical scissor or forceps. The surgeon input console 114 may also include one or more foot pedals (not shown) that may be actuated by the surgeon to initiate various other operations. For example, a foot pedal may be configured to generate a clutch signal for temporarily decoupling the surgical instruments 102-108. A foot pedal may also be configured to initiate delivery of energy, such as generate electrocautery signals for initiating delivery of an electrocauterization current to an instrument, to cut, cauterize, or coagulate tissue (which can involve resection of tissue, vaporization of tissue, or coagulation of tissue). Delivery of energy can include delivery of ultrasonic energy (such as, with a harmonic scalpel instrument), delivery of electric energy (such as, with an electrocautery instrument), delivery of laser energy (such as, with a cautery instrument), delivery of radio frequency energy (such as, with a cautery instrument), or the like. These other input signals also need to be delivered to the robotic surgery system 100 to initiate their respective operations. Additionally, the robotic surgery system 100 may generate event-oriented notifications such as notifications of error conditions that must be communicated to the physician input console 114 to update the physician 112. Event-oriented messages may be time-sensitive, but are not necessarily synchronous.

The physician input console 114 also includes a display 120 for displaying images generated by the in-patient imaging system. The in-patient imaging system would generally be implemented as a high-resolution imaging system (such as, a video camera) that generates a stream of image frames. In some instances, the imaging system may generate images from differing perspectives that convey three-dimensional information and the display 120 may be configured as a stereoscopic display. The display signals generated by the imaging system are transmitted over an image transmission cable 122 back to the physician input console 114 for driving the display 120. The image transmission cable 122 is generally selected to ensure that the image frames are delivered to the display in near real-time so that the physician 112 does not perceive any delay between their hand movements and movements of the surgical instruments 102-108 represented on the display. In some implementations, the input signals and display signals may both be transmitted over a single shared cable or bus.

A connection 115 can be used for transmission of data between the robotic surgery system 100 and the surgeon input console 114. As illustrated in FIG. 1, the connection 115 can utilize the control cable 118 and the image transmission cable 122. The connection 115 can be a direct connection that links the robotic surgery system 100 and the surgeon input console 114. The connection 115 can be isolated from any other network. For instance, the connection 115 can be a direct local area network (LAN) connection.

The robotic surgery system 100 may be housed within a sterile operating room that forms part of an operating suite. The surgeon or another surgeon aided by a perioperative nurse may make the necessary incisions and insert the instruments 102-108. The surgeon input console 114 may be housed in a portion of the operating suite that is separated from the operating room so that the surgeon operating the input console need not wear surgical gloves while manipulating the controls of the input console. The cables 118 and 122 would generally extend through a port in a wall between the surgeon input console 114 and the robotic surgery system 100. In cases where another surgeon performs the incisions in the body of the patient 110, the operating surgeon may not need to complete the full process of scrubbing, gowning, and gloving before the operation. In this situation, the surgeon input console 114 however remains in a direct wired connection with the robotic surgery system 100 via the cables 118 and 122. The direct wired connection ensures that the robotic surgery system 100 is able to rapidly respond to the surgeon's inputs provided at the surgeon input console 114 and the display 120 displays images of the surgical site with a negligible delay that is virtually unnoticeable to the surgeon.

Overview of Remotely Controlling Robotic Procedures

While certain examples are described in the context of remotely controlling a surgical procedure performed by a robotic surgery system, the approaches described herein can be used for remotely controlling a variety of medical procedures, including invasive and non-invasive procedures as well as surgical and non-surgical procedures. The approaches described herein can be used for remotely controlling surgical procedures, interventional procedures, or diagnostic procedures (such as, procedures not involving manipulation of tissue). Medical procedures can be performed by patient-side robotic procedure systems that are controlled by physician-side robotic procedure consoles. Patient-side robotic procedure systems can have one of more features of the robotic surgery systems described herein, such as one or more of an imaging system on a robotic arm or an instrument on a robotic arm. Physician-side robotic procedure consoles described herein can have one or more features of the input consoles described herein, such as one or more displays and input devices.

One of the main problems in the healthcare industry is the lack of physicians (for instance, surgeons) and their underutilization. On one hand, there is a lack of high-quality physicians. For instance, a 2022 article by the American College of Surgeons concludes that there is an acute ongoing shortage of surgeons available in the United States to serve the patient population. The shortage of high-quality surgical care is particularly severe in rural areas. In addition, surgeons in many geographical areas may not have access to a sufficient volume of patients to perfect their surgical skills because the population is not evenly distributed, thus creating a lack of surgical volume in such areas. On the other hand, currently there are severe inefficiencies with utilizing the time of physicians. For instance, surgeons are required to travel between different hospitals, some of which may be located in difficult to reach places or between different operating rooms in a single hospital. Moreover, surgeons are required to wait for patients and operating rooms to be prepared for surgery. This results in a serious underutilization of surgeons' time. There are many advantages in allowing surgeons to control robotic surgery systems (such as, the system 100) from remote locations in order to increase efficiency and improve patient care. For surgeons, remote surgery facilitates optimal utilization of their time and provides access to a sufficient volume of patients to perfect their skills. For patients, remote surgery creates ample access to the right surgeon and the right care at an affordable price, decreases the need for travel, and decreases delayed care. However, there are a number of challenges with designing a system that would allow remotely controlling robotic surgery systems. These include transmission delay, availability, and reliability of transmission.

Figure 2:
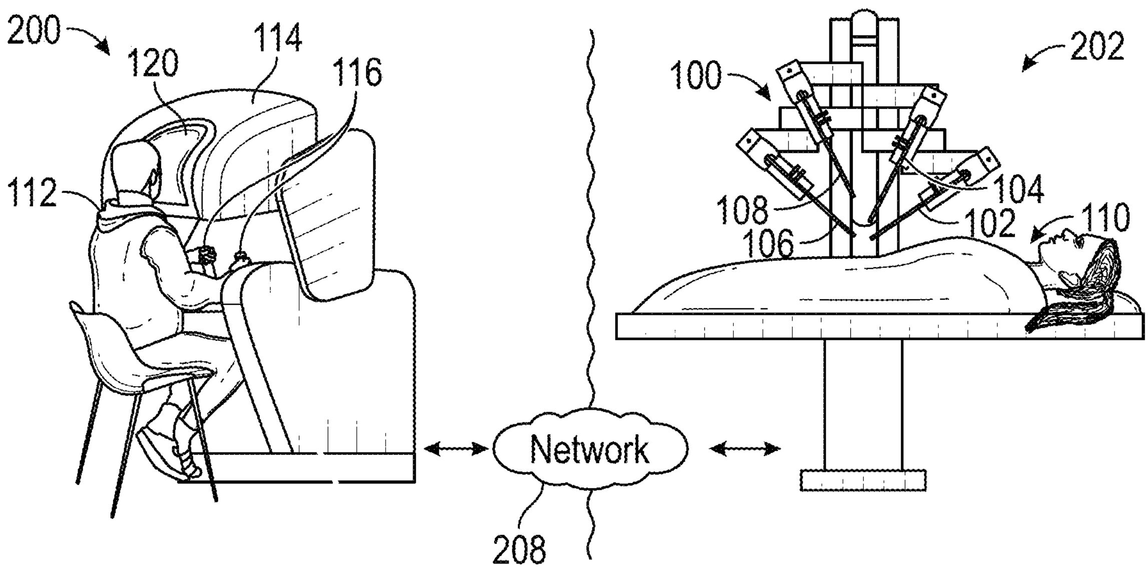
FIG. 2 is perspective view of a robotic surgery system.

Referring to FIG. 2, the surgeon input console 114 is disposed at a surgeon-side location 200 and the robotic surgery system 100 shown in FIG. 1 is disposed at a patient-side location 202. The surgeon-side location 200 is remote from the patient-side location 202 to an extent where a directly wired connection between the robotic surgery system 100 and the surgeon input console 114 is no longer possible. Advantageously, the surgeon-side location 200 may be in another building or even another city, state, or country. In this example, communication is performed between the surgeon-side location 200 and the patient-side location 202 via a network 208, and there is no direct connection 115 between the surgeon input console 114 and the robotic surgery system 100.

Figure 3:
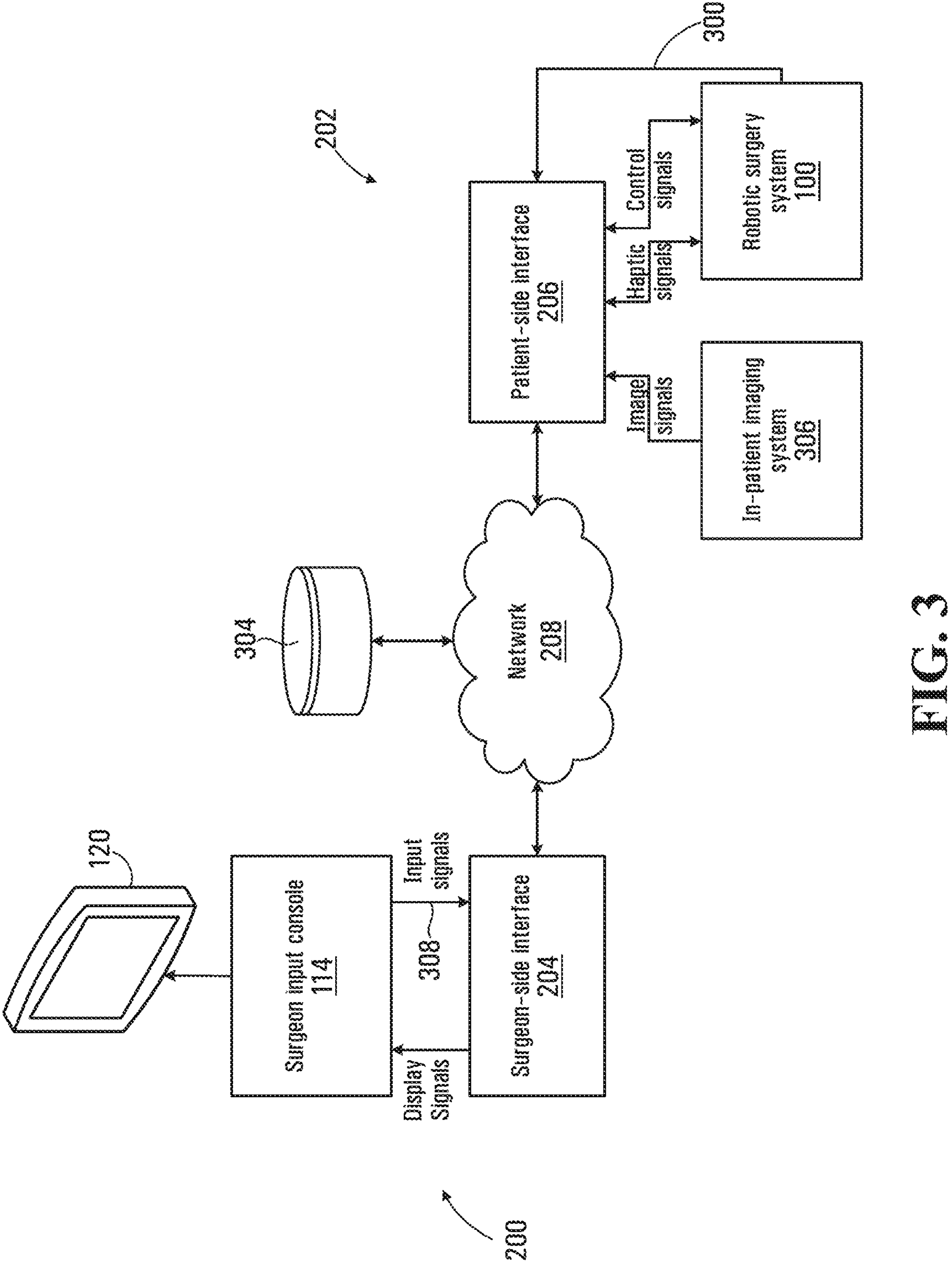
FIG. 3 is a block diagram of components of the robotic surgery system of FIG. 2.

Referring to FIG. 3, communication between the surgeon-side location 200 and patient-side location 202 are conducted via a surgeon-side interface 204 and a patient-side interface 206, which are shown schematically in FIG. 3. The surgeon-side interface 204 is connected to receive input signals from the surgeon input console 114. For example, the surgeon input console 114 may generate a stream of motion input signals 308 that represent the instantaneous position of the handles 116 within an input console workspace. Motion input signals can represent a desired movement (including position and velocity) of an instrument in the input console workspace. These motion input signals will generally be transformed via kinematic processing into signals representing desired positions and orientations of the joints of the instruments 102-108 within a surgical workspace of the robotic surgery system 100. In some instances, kinematic processing translates the position and movement of the handles 116 within the input console workspace into the position and movement of joints of the instruments 102-108. The translation can be performed by transforming the position and orientation of the handles 116 in the Cartesian coordinate system to the coordinates of the joints of the instruments 102-108 in the surgical workspace and vice versa. Other processing functions may then be used to transform these kinematically derived instrument joint positions into drive signals for actuating various actuators, such as motor servos, that cause movement of the instruments 102-108 within the surgical workspace. In the system shown in FIG. 1, the kinematic and other processing may be implemented within the surgeon input console 114 or the within robotic surgery system 100. In the implementation of FIG. 3, the input signals 308 can be picked up directly from the input devices of the surgeon input console 114 and before any kinematic or other processing has been performed. For some robotic surgery system 100, the input signals are generated by the input devices of the surgeon input console 114 at a relatively low frequency (or rate of change), for example about 200 Hz or every 5 milliseconds or about 30 Hz or less. The input signals 308 thus require a relatively low bandwidth or data rate for transmission. In contrast, post-kinematics and other processing signals may have a significantly higher frequency (or rate of change). As an example, in some robotic surgery systems the servo rate at the motor controller may be in the region of about 10 kHz or more, which may require a significantly higher bandwidth or data rate for transmission than the motion input signals generated at the input device.

In general, remotely controlling a robotic surgery system can be achieved by transmitting from the surgeon-side interface 204 to the patient-side interface 206 a complete set of signals that control the instruments 102-108 (which include at least one imaging system). Such signals may be referred to as control signals. To reduce delay and guarantee reliability of the transmission, such set of signals can include signals having the lowest frequency (or rate of change) among a plurality of available signals. As described above, input signals 308 can be transmitted from the surgeon-side interface 204 to the patient-side interface 206, rather than signals generated as a result of kinematic processing that generates signals representing desired coordinates of the joints of the instruments 102-108 in the surgical workspace associated with the robotic surgery system 100 or the drive signals (such as, torque) for actuating the motors of the instruments 102-108. In some cases, the surgeon-side interface 204 can select input signals 308 for transmission from the plurality of available signals, which can include signals generated as a result of kinematic processing and the drive signals.

In certain implementations, one or more signals generated as a result of kinematic processing may be transmitted by the surgeon-side interface 204 to the patient-side interface 206. These signals can be transmitted along with the input signals 308.

The physician-side interface 204 is in communication with the patient-side interface 206 over the network 208. The patient-side interface 206 is in communication with the robotic surgery system 100 for receiving and delivering control signals to the robotic surgery system. The patient-side location 202 also includes an in-patient imaging system 306, which generates images of the surgical site within the patient. As described above, one of the surgical instruments 102-108 may be configured to generate the in-patient images or a separate imaging system may be employed. The in-patient imaging system 306 generates data representing image frames, which is encoded into an image data stream by the patient-side interface 206 and transmitted over the network 208 to the physician-side interface 204. Image data can be encoded using hardware circuitry of the patient-side interface 204, such as one or more processors, one or more graphics processing units (GPUs), one or more field-programmable gate arrays (FPGAs), or one or more application-specific integrated circuits (ASICs). Image data can include different types of images obtained by different imaging systems. For example, image data can include endoscopic image (or video) data and X-ray images obtained by a fluoroscopy imaging system. Image data can alternatively or additionally include X-ray images obtained by a radiography imaging system, CT images obtained by a CT imaging system, ultrasound images obtained by an ultrasound imaging system, or MRI images obtained by an MRI imaging system. Different types of image data can be encoded into the image data stream for transmission over the network 208 to the physician-side interface 204. The physician-side interface 204 receives and decodes the image data stream to recover the image frame data, which is sent via the physician input console 114 to the display 120 associated with the physician input console 114. The physician 112 is able to view the surgical site on the display 120 and cause movements of the handles 116 of the physician input console 114, which are encoded by the input devices and delivered as control signals to the patient-side interface 206.

The robotic surgery system 100 may be additionally configured to generate haptic feedback and/or force feedback signals. In robotic surgery, haptic feedback signals may be generated to alert the physician 112 when an attempt is made to move one of the instruments 102-108 against an instrument movement boundary or other impediment to motion. Haptic signals may also be generated when two of the instruments 102-108 are moved toward a collision condition. These haptic signals are generally used to deliver haptic feedback via the handles 116 of surgeon input console 114 that alert the surgeon 112 to the condition. Additionally, some robotic systems may also be configured to generate force feedback signals that can be used to deliver force feedback to the surgeon via the input console 114. The force feedback may serve to indicate that the surgeon 112 is attempting to move one of the instruments 102-108 against a limitation such as human tissue or an organ. In some implementations the patient-side interface 206 may be configured to receive the haptic or force feedback signals and transmit the signals back to the surgeon-side interface 204 for delivery to the surgeon input console 114.

The network 208 may be provided as a connection to the Internet. In some cases, the network 208 may be a dedicated network such as a point-to-point fiber or a specially-conditioned and monitored network that aims to reduce transmission delay and increase reliability and stability. The network 208 can be a wide-area network (WAN). The surgeon-side interface 204 is in communication with the robotic surgery system 100 at the patient-side location 202 via the network 208.

A data store 304 can be included in communication with the network 208. The data store 304 may be used as remote network storage for storing data logs and other information connected with surgical operations performed by the systems shown.

The robotic surgery system 100 may from time-to-time generate event-oriented notifications at the patient-side location. Each event-oriented notification at the patient-side location 202 may be processed to generate a notification record including a timestamp indicating a time at which the event-oriented notification was generated, status information including information indicating a processing status of the event-oriented notification, and timeout information including information indicating an expiry time by which the event-oriented notification should be processed. These notification records are then transmitted to the surgeon-side location 200. At the surgeon-side location 200, each notification record is received and accumulated for processing. When the status in the notification record indicates that the notification record has not yet been communicated to the surgeon input console and the expiry time in the timeout information exceeds the current time at the surgeon-side location 200 (for instance, as maintained by the surgeon-side interface 204), an alert is generated. When the status indicates that the notification record has not yet been communicated to the surgeon input console and the expiry time does not yet exceed the current time at the surgeon-side location 200, a notification message is generated and communicated to the surgeon input console. The status in the notification record is then changed to indicate that the notification record has been processed.

In some implementations, the robotic surgery system 100 may be expecting the control signals to be provided at a certain threshold rate (such as, the rate of a patient-side synchronization signal (PSS) signal 300). When the control signals received by the robotic surgery system do not satisfy such threshold rate, the patient-side interface 206 can repeat at least some of the received control signals or otherwise modify the control signals in order to provide the control signals to the robotic surgery system 100 at the threshold rate. The threshold rate may not be satisfied as a result of control signals not being received by the patient-side interface 206 at a sufficient rate (because of, for instance, network delay) or due to one or more control signals having been discarded, among others.

In certain cases, the robotic surgery system 100 can transmit acknowledgment information to the surgeon input console 114, for instance, in response to receiving control signals. Acknowledgment information can be transmitted as an acknowledgment signal or message. For example, the robotic surgery system 100 may acknowledge each control signal message or packet with an acknowledgment message. The surgeon input console 114 may be expecting the acknowledgment message to be provided at a certain threshold rate (for instance, corresponding to the rate of transmission of packets to the patient-side location 202). When the acknowledgment messages received by the surgeon input console do not satisfy such threshold rate, the surgeon-side interface 204 can repeat at least some of the received acknowledgment messages or otherwise modify the acknowledgement messages in order to provide the acknowledgment messages to the surgeon-side interface 204 at the threshold rate. The threshold rate may not be satisfied as a result of acknowledgment messages not being received by the surgeon-side interface 204 at a sufficient rate (because of, for instance, network delay) or due to one or more acknowledgment messages having been discarded, among others.

Figure 5:
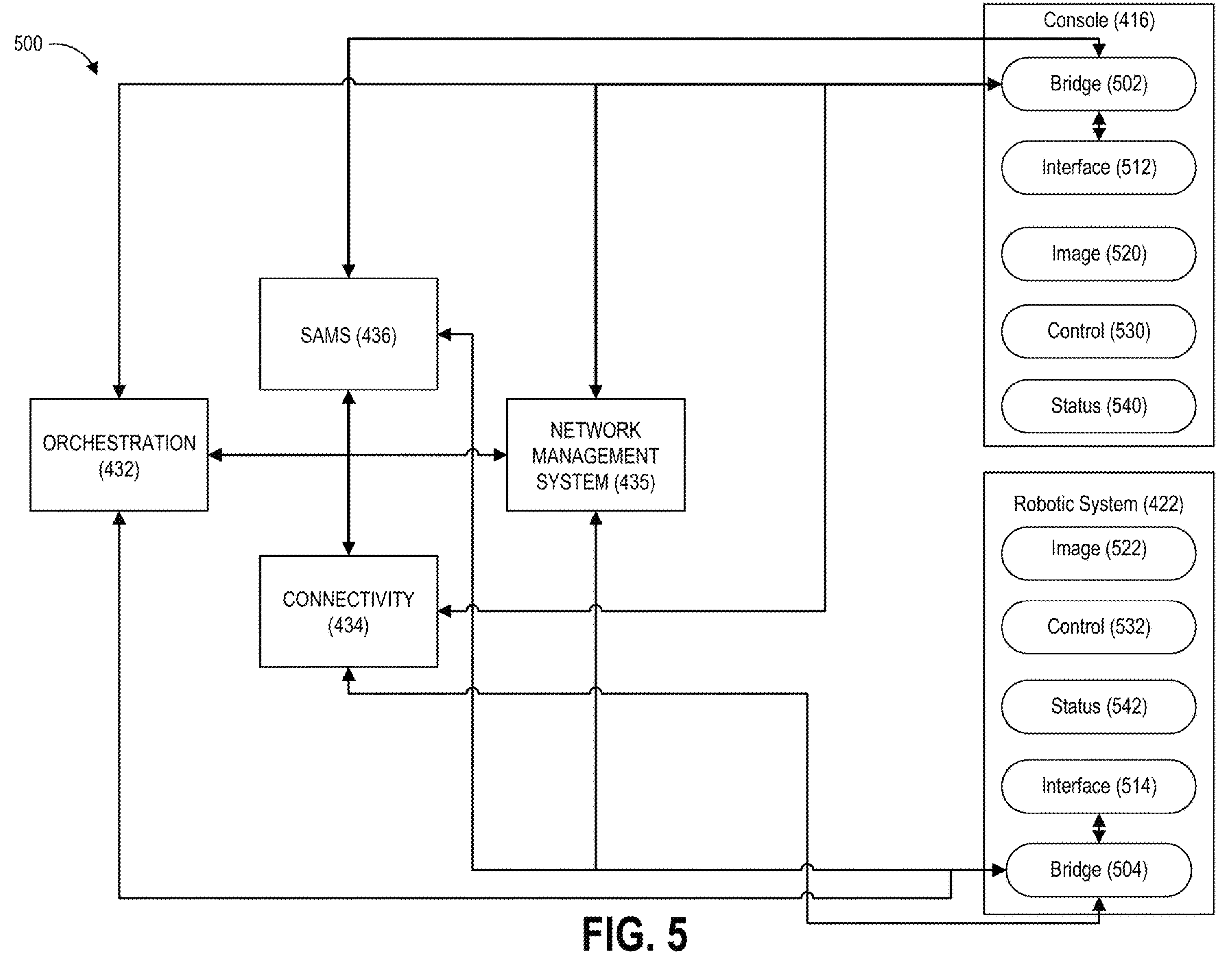
FIG. 5 is a schematic view of a remote robotic-assisted medical system.

The surgeon-side interface 204 can be integrated with the surgeon input console 114, which can encompass being wholly separate from the surgeon input console 114 or being wholly or partially a portion of the surgeon input console 114. In some implementations, the surgeon-side interface 204 can be implemented as software and/or firmware being executed by one or more processors of the surgeon input console 114. For instance, FIG. 5 illustrates a surgeon input console 416 that implements software and/or firmware interface 512 that provides functionality of the surgeon-side interface 204.

The patient-side interface 206 can be integrated with the robotic surgery system 100, which can encompass being wholly separate from the robotic surgery system 100 or being wholly or partially a portion of the robotic surgery system 100. In some implementations, the patient-side interface 206 can be implemented as software and/or firmware being executed by one or more processors of the robotic surgery system 100. For instance, FIG. 5 illustrates a robotic surgery system 422 (or robot 422) that implements a software and/or firmware interface 514 that provides functionality of the patient-side interface 206.

System for Remotely Controlling Robotic Procedures

Figure 4:
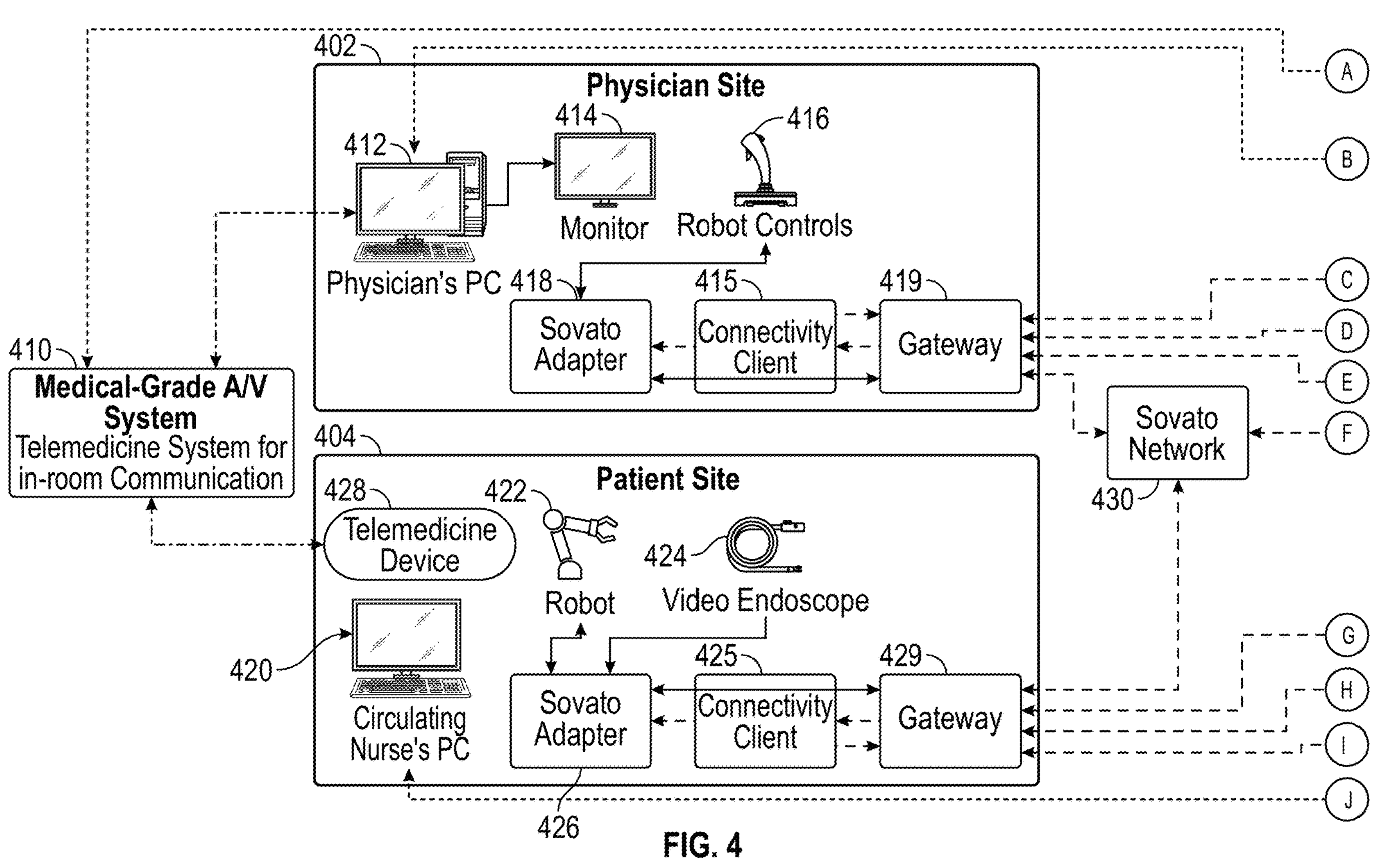
FIG. 4 is a schematic view of a remote robotic-assisted medical system.
Figure 4:
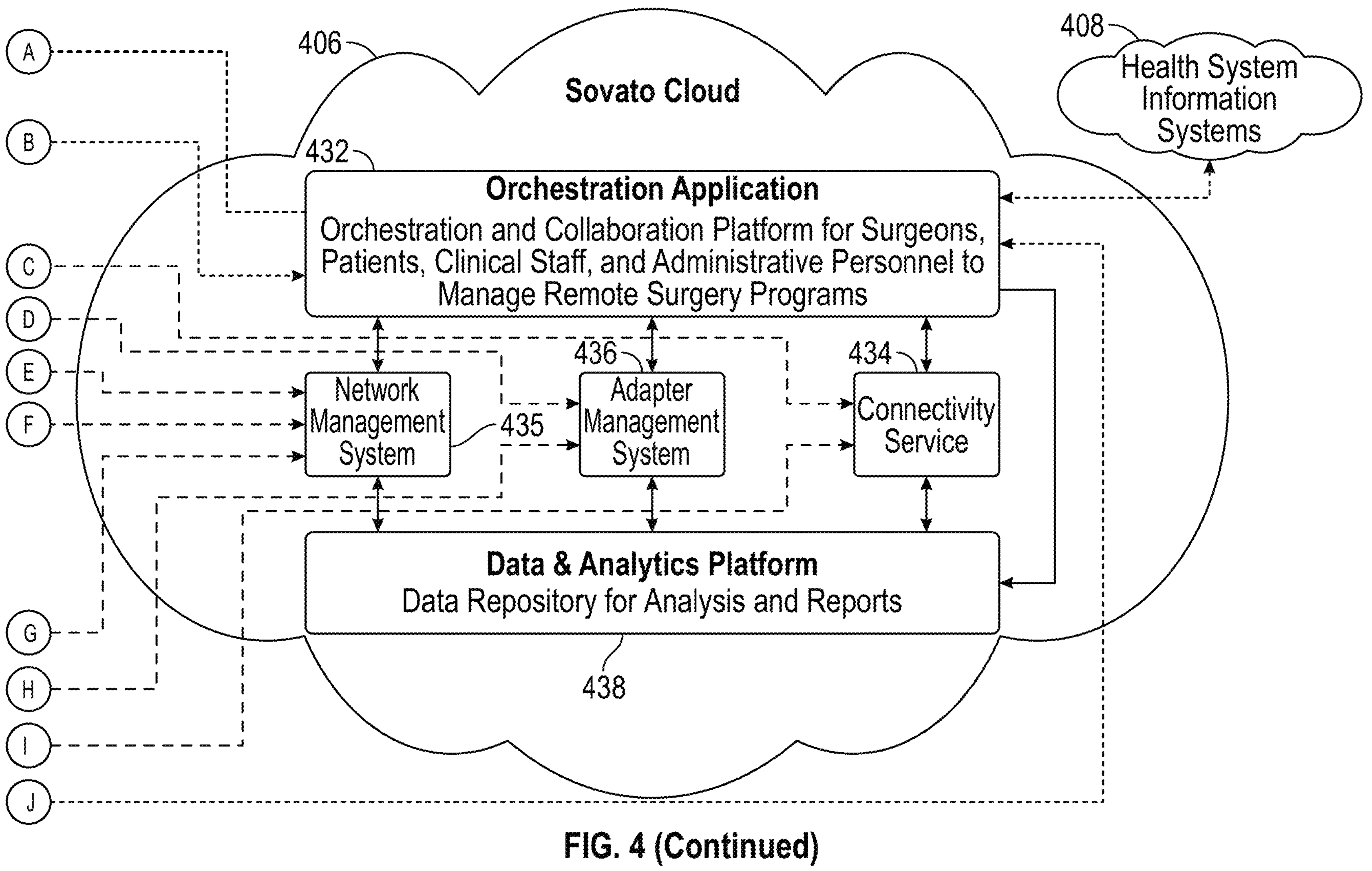

FIG. 4 illustrates a schematic view of a remote robotic-assisted medical system 400. The system 400 can include one or more physician sites 402 each having one or more computing devices 412 (such as, one or more physician personal computers (PCs)), one or more monitors 414 (which can be connected to the one or more physician PCs), one or more physician-side connectivity clients 415, one or more robot control and display systems 416 (which can be, for instance, same as or similar to the surgeon input console 114 and can be referred to as the physician input console 416), one or more physician-side adapters 418 (which can be, for instance, same as or similar to the surgeon-side interface 204), and a physician-side gateway 419. Any of the computing devices described herein can be mobile or portable.

The system 400 can further include one or more patient sites 404 (for instance, medical centers or hospitals) each having one or more computing devices 420 (such as, one or more nurse PCs), one or more medical procedure robots 422 (which can be, for instance, same as or similar to the robotic surgery system 100, and can be referred to as robot), one or more imaging systems 424 (such as, a video endoscope) that can be part of the robotic surgery system, one or more patient-side connectivity clients 425, one or more patient-side adapters 426 (which can be same as or similar to the patient-side interface 206), and a patient-side gateway 429. The system 400 can also include one or more telemedicine devices 428 configured to communicate telemedicine information and provide the physician with audio and video related to any procedures the physician is performing. The system 400 can further include a network 430 (which can utilize the network 208 as is further explained in connection with FIG. 6) connecting a physician-side adapter 418 to a patient-side adapter 426.

In some cases, as described herein, a physician-side adapter 418 can be integrated with a robot control and display system 416 and/or a patient-side adapter 426 can be integrated with a robot 422. In some instances, a physician PC 412 can be integrated with a robot control and display system and/or a nurse PC 420 can be integrated with a robot 422. Being integrated with can encompass being wholly separate from a corresponding system or being wholly or partially a portion of the corresponding system. For instance, being integrated with can encompass being implemented as software and/or firmware being executed by one or more processors of the corresponding system.

The system 400 can include one or more computing devices, which can form a computing cloud 406. The cloud can implement one or more of: an orchestration server or application 432, a connectivity server 434, a network management system 435 (NMS) (sometimes referred to as network control system or NCS), an adapter management server or system 436 (sometimes referred to as SAMS), and a data and analytics server or platform 438. The system 400 can further include a health system information systems 408, comprising a database storing electronic health records (EHR) and/or electronic medical records (EMR) relating to one or more patients. The system 400 can further include one or more medical-grade audio/visual (A/V) systems 410, which can communicate with one or more telemedicine devices 428.

As described herein, the orchestration application 432 can perform one or more of: verify credentials of a physician, provide coordination between the patient side and physician side (or verify that such coordination has been established), establish an A/V connection between the physician side and the patient side (or verify that the A/V connection has been established), verify that a time window for remotely performing a medical procedure on the patient is open, and verify that network connection satisfies one or more conditions. As described herein, the connectivity server 434 can track network addresses of the physician-side adapters 418 and the patient-side adapters 426 and establish a connection between a physician-side adapter and a patient-side adapter. As described herein, the adapter management system 436 can perform adapter monitoring and management. For example, the health of the adapters can be verified and tracked.

A physician PC 412 can be operably connected to a medical-grade A/V system 410 and the orchestration application 432. In an example, the physician PC 412 can communicate telemedicine information and provide the physician with audio and video related to any robotic procedures the physician is conducting. For example, the physician PC 412 can display to the physician on a monitor 414 a real-time video of a patient site 404, the premises where a medical procedure will take place, is being performed, or has been performed. The monitor 414 can display such footage in response to the medical-grade A/V system 410 providing video footage of the patient site 404 to the physician site 402. The physician PC 412 can also be operably connected to the orchestration application 432. The physician PC 412 can transmit physician related information to the orchestration application 432. The physician related information can include information such as the physician's credentials, identification, schedule, specialties, and any access related information related to the robotic procedures the physician will perform. In some implementations, a single physician PC 412 can be used for multiple physician input consoles 416. In some cases, each physician input console 416 can have a dedicated physician PC 412 (for instance, such dedicated physician PC 412 can be connected to the physician input console 416 or its associated physician-side adapter 418 via a wired or wireless connection).

A physician-side connectivity client 415 can allow a physician-side adapter 418 to connect to the network 430 and cloud 406. The physician-side connectivity client 415 can be implemented in software and/or firmware being executed by one or more processors of the physician-side adapter 418. The physician-side connectivity client 415 can call one or more application programming interfaces (APIs) to connect the physician-side adapter 418 to one or more of the network management system 435, the adapter management system 436, or the connectivity server 434. In some instances, the physician-side connectivity client 415 may be implemented by a computing device that is separate from the physician-side adapter 418. In implementations that integrate the physician-side adapter 418 with the physician input console 416, the physician-side connectivity client 415 can be implemented by the physician input console 416.

A physician-side connectivity client 415 (or a physician-side adapter 418) can be assigned an internal internet protocol (IP) address and an external IP address. The internal IP address can correspond to an IP address with respect to a local network of a physician site 402. The external IP address can correspond to an IP address outside of that local network (such as, IP address on the network 430). The physician-side connectivity client 415 can communicate with the cloud 406 via the network 430 and provide information (such as, the internal IP address and the external IP address) to initiate a connection with a patient-side connectivity client 425. The information to initiate a connection with the patient-side connectivity client 425 can include one or more of: an identifier of the physician-side adapter 418, an internal IP address of the physician-side connectivity client 415, or any or information needed to establish a connection with the patient-side connectivity client 425.

A physician input console 416 can include a visual display to show the physician visual indications relating to the robotic procedure. The physician input console 416 can be operably coupled to a physician-side adapter 418. The physician input console 416 can display a view of the robotic procedure site (for instance, as detected by an imaging system 424) and/or any other component relevant to the robotic procedure. A monitor 414 can display visual indicators representing a strength of signal connectivity to the components in the patient site 404. In another example, the monitor 414 can display device characteristics regarding the physician input console 416 and/or the robot 422.

As described in connection with a physician input console 114, a physician input console 416 can include one or more devices used to control one or more medical procedure robots. The physician input console 416 can be operably coupled to a physician-side adapter 418. In an example, robot controls of the physician input console 416 can control movement, actuation, clutch, or any other relevant feature for a medical procedure robot to perform robotic procedures. The physician input console 416, and the corresponding console, can include a type. The type can correspond to the manufacturer of the physician input console, model of the physician input console, and/or version of the software or firmware being executed by one or more processors or the physician input console 416. For example, the manufacturer of the physician input console 416 can include Intuitive Surgical, Medtronic, or any other manufacturer of a physician input console. As another example, the model of the physician input console 416 can include Da Vinci Xi, Da Vinci X, or Da Vinci SP manufactured by Intuitive Surgical.

A physician-side adapter 418 can include a physical device, program, application, application programming interface (API), software development kit (SDK), or another device or program to allow remote robotic procedure. In some implementations, the physician-side adapter 418 can be software and/or firmware being executed by one or more processors of a physician input console 416. The physician-side adapter 418 can be operably coupled to a patient-side adapter 426 via the network 430 and/or the cloud 406, including the connectivity server 434 and the adapter management system 436. In an example, the physician-side adapter 418 can include a device operably coupled to the physician input console 416, to interface the physician input console 416 to the cloud 406 and the network 430. In this example, the physician-side adapter 418 can include hardware components and software components to receive communication signals from the physician input console 416. In this example, the physician-side adapter 418 (or a physician-side connectivity client 415) can include an internal internet protocol (IP) address. The internal IP address can correspond to an IP address with respect to a local network of a physician site 402.

A physician-site adapter 418 and/or a patient-side adapter 426 can be configured software-defined wide-area network (SD-WAN) devices. The network 430 can be configured as SD-WAN network connecting such SD-WAN devices. Internal IP addresses can be used to communicate with devices on the SD-WAN. The internal IP address can be used to establish the connection for remote robotic procedure since the adapters would be part of the same WAN, and external IP addresses may not need to be used. Any other components of the system 400, such as an A/V system 410, physician PC 412, nurse PC 420, or telemedicine device 428, can be similarly configured as SD-WAN devices and become part of the SD-WAN.

Physician-side gateway 419 can forward network traffic between one or more physician-side connectivity clients 415 at a physician site 402 and the network 430. A physician-side connectivity client 415 can be connected to the physician-side gateway 419 via a suitable network connection available at the physician site 402, such as LAN (for instance, implemented using Ethernet or Wi-Fi). In some instances, the physician-side gateway 419 may not be present, and the physician-side connectivity client 415 can be directly connected to the network 430.

When multiple physician input consoles 416 are present at the physician site 402, each can be connected directly or through one or more of its dedicated physician-side adapter 418 or physician-side connectivity client 415 to the physician-side gateway 419 via a dedicated network connection (such as, via a dedicated Ethernet cable plugged into a port in the physician-side gateway 419). This dedicated network connection can be a LAN. In this arrangement, no physician input console shares, at a physician site, any network connection (such as, LAN) with any other physician input console and each physician input console has its own dedicated network connection to a physician-side gateway. The physician-side gateway 419 can be a single gateway with sufficient number of ports to connect all physician input consoles or a collection of gateways.

A nurse PC 420 can also be operably connected to the orchestration application 432. The nurse PC 420 can transmit patient related information to the orchestration application 432. The patient related information can include the patient's health records, identification, schedule, notes, and any access related information related to the robotic procedures the patient can receive. In some implementations, a single nurse PC 420 can be used for robots 422. In some cases, each robot 422 can have a dedicated nurse PC 420 (for instance, such dedicated nurse PC 420 can be connected to the robot 422 or its associated patient-side adapter 426 via a wired or wireless connection).

A robot 422 can include one or more robotic devices used to perform robotic procedures. The robot 422 can be operably coupled to a patient-side adapter 426. In an example, the robot 422 can receive controls to perform movement, actuation, power, and any other relevant feature to perform a robotic procedure. The robot 422, and any corresponding devices, can include a type. The type can correspond to the manufacturer of the robot, model of the robot, and/or version of the software or firmware being executed by one or more processors of the robot 422. For example, the manufacturer of the robot 422 can include Intuitive Surgical, Medtronic, or any other manufacturer of medical procedure robots. As another example, the model of the robot 422 can include Da Vinci Xi, Da Vinci X, or Da Vinci SP manufactured by Intuitive Surgical.

An imaging system 424 can communicate video to the physician related to any robotic procedures the physician is performing. The imaging system 424 can be operably coupled to the patient-side adapter 426 (directly or through the robot 422). In an example, the imaging system 424 can provide to the physician site 402 a view of a robotic procedure site. The view can include a real-time perspective of the patient before, during, or after robotic procedure is performed.

A patient-side connectivity client 425 can allow a patient-side adapter 426 to connect to the network 430 and cloud 406. The patient-side connectivity client 425 can be implemented in software and/or firmware being executed by one or more processors of the patient-side adapter 426. The patient-side connectivity client 425 can call one or more APIs to connect the patient-side adapter 426 to one or more of the network management system 435, the adapter management system 436, or the connectivity server 434. In some instances, the patient-side connectivity client 425 may be implemented by a computing device that is separate from the patient-side adapter 426. In implementations that integrate the patient-side adapter 426 with the robot 422, the patient-side connectivity client 425 can be implemented by the robot 422.

A patient-side connectivity client 425 (or a patient-side adapter 426) can include an internal IP address and an external IP address. The internal IP address can correspond to an IP address with respect to a local network of a patient site 404. The external IP address can correspond to an IP address outside of that local network (such as, IP address on the network 430). The information to initiate a connection with the physician-side connectivity client 415 can include one or more of: an identifier of the patient-side adapter 426, an internal IP address of the patient-side connectivity client 425, or any other information needed to establish a connection with the physician-side connectivity client 415.

A patient-side adapter 426 can be operably coupled to a physician-side adapter 418 via the network 430 and/or the cloud 406. The patient-side adapter 426 can include one or more of a physical hardware, program, application, API, SDK, or another device or program to allow remote robotic procedures. For example, patient-side adapter 426 can include a device operably coupled to a robot 422 to interface the robot 422 to the cloud 406 and the network 430. In this example, the patient-side adapter 426 can include hardware components and software components to receive communication signals from the robot 422 and establish a network connection to the network 430 and the cloud 406. In some implementations, the patient-side adapter 426 can be software and/or firmware being executed by one or more processors of the robot 422. Similarly to a physician-side adapter 418, the patient-side adapter 426 can include an internal IP address and an external IP address. As described herein, one or more of such IP addresses can be utilized to establish a connection with the physician-side adapter. The information to initiate a connection with the physician-side adapter 418 can include an identifier of the patient-side adapter 426, an internal IP address of the patient-side adapter 426, an external IP address of the physician-side adapter 418, and/or any or information relevant to establish a connection with the patient-side adapter 426. As described herein, the patient-side adapter 426 can be configured as SD-WAN device and its internal IP address can be used to establish the connection.

A telemedicine device 428 can communicate telemedicine information and provide a physician with audio and video related to any robotic procedures the physician is performing. The telemedicine device 428 can be operably coupled to a medical-grade A/V system 410. In an example, the telemedicine device 428 can provide to the physician site 402 a view of the patient site 404 (such as, an operating room). The view can include a real-time perspective of the patient before, during, or after a procedure is performed. In another example, the telemedicine device 428 can receive information from a physician PC 412 through the medical-grade A/V system 410. For example, the telemedicine device 428 can receive information related to the procedure, including one or more of a notice regarding the physician's readiness, status of connectivity, updated patient health records, or scheduling information. In this example, the related information can include the physician's credentials, identification, schedule, specialties, and any access related information related to the robotic procedures the physician will perform. In another example, the telemedicine device 428 can further include an A/V system including a third-party telemedicine hardware provider and medical cart. The A/V system 410 and/or the telemedicine device 428 can facilitate provision of an audio and/or video feed from the patient site 404 to a physician site 402 (and vice versa) as well as facilitate a two-way audio and/or video communication between the patient site 404 and the physician site 402. In some instances, a two-way audio communication between the patient site 404 and the physician site 402 and a one-way video communication from the patient site 404 to the physician site 402 can be utilized.

Patient-side gateway 429 can forward network between one or more patient-side connectivity clients 425 at a patient site 404 and the network 430. A patient-side connectivity client 425 can be connected to the patient-side gateway 429 via a suitable network connection available at the patient site 404, such as LAN. In some instances, the patient-side gateway 429 may not be present, and the patient-side connectivity client 425 can be directly connected to the network 430.

When multiple robots 422 are present at the patient site 404, each can be connected directly or through one or more of its dedicated patient-side adapter 426 or patient-side connectivity client 425 to the patient-side gateway 429 via a dedicated network connection (such as, via a dedicated Ethernet cable plugged into a port in the patient-side gateway 429). This dedicated network connection can be a LAN. In this arrangement, no robot shares, at a patient site, any network connection (such as, LAN) with any other robot and each robot has its own dedicated network connection to a patient-side gateway. The patient-side gateway 429 can be a single gateway with sufficient number of ports to connect all robots or a collection of gateways.

The network 430 can connect the physician-side adapter 418 and the patient-side adapter 426. The network 430 can be configured as SD-WAN to provide connectivity between the physician-side adapter 418 and the patient-side adapter 426. The network 430 can facilitate a peer-to-peer connection between a physician-side adapter 418 and a patient-side adapter 426. Such peer-to-peer connection can allow the physician-side adapter 418 and the patient-side adapter 426 to transmit and receive information and instructions (such as, in the form of data packets) directly. The information can include robot control instructions and feedback sensor information, real-time patient information including medical health monitoring statuses, patient-side video endoscope content (for example, from the imaging system 424), network connectivity strength including a primary and alternate network connectivity options (for example, SD-WAN, 5G, Ethernet, fiber optic, satellite communication, or any other type of connection available), and any other information relevant to the peer-to-peer network connection.

There can be several ways for establishing a connection via the network 430. For example, a physician-side adapter 418 can request connection to a patient-side adapter 426 from the connectivity server 434. For example, the physician-side adapter 418 can transmit a request to the connectivity server 434 and receive the patient-side adapter 426 internal IP address from the connectivity server 434. In this example, the physician-side adapter 418 can then request to establish a connection (such as, a direct peer-to-peer connection) with the patient-side adapter 426.

As another example, a physician-side adapter 418 can request a connection to a patient-side adapter 426 from the adapter management system 436. For example, the physician-side adapter 418 can transmit a request to the connectivity server 434 and receive the patient-side adapter 426 internal IP address from the adapter management system 436. In this example, the physician-side adapter 418 can then request to establish a connection (such as, a direct peer-to-peer connection) with the patient-side adapter 426.

While these examples describe that the physician-side adapter 418 initiates the connection to the patient-side adapter 426, the patient-side adapter 426 can similarly initiate the connection in some implementations.

In any of these examples, external IP address(es) can also be used to establish the connection. As described herein, external IP address(es) can be used when the adapters are not part of the same network (such as, not part of the same SD-WAN).

The connection can be established in response to: 1) verification of login credentials of a physician, 2) completion of coordination between the physician side and patient side (such as, completion of one or more handshake protocols), 3) establishment of a two-way audio communication between the physician side and the patient side, 4) establishment of a video communication from at least the patient side to the physician side, 5) verification of compatibility of physician input console and robot, and 6) verification that the network connection satisfies one or more network conditions (such as, one or more of a network latency threshold, network jitter threshold, network packet loss threshold, and network bandwidth threshold). In some instances, the connection can be established in response to ensuring that at least one of the foregoing conditions, at least two of the forgoing conditions, at least three of the foregoing conditions, at least four of the foregoing conditions, or all of the foregoing conditions have been satisfied. In some cases, the orchestration application 432 can perform the verifications.

A connection establishment protocol can be implemented to form the connection. The connection establishment protocol can be coordinated by the orchestration application 432, for instance, responsive to a request to start a session received from a patient side or physician side. The request can be received through a user interface provided by a physician PC 412 or nurse PC 420. Responsive to the request, conditions for establishing the connection can be verified (as described herein). After it has been verified that the connection can be established, the orchestration application 432 can transmit a request to initiate the connection. The request to initiate the connection can include identifiers of a physician-side adapter 418 and patient-side adapter 426 (for instance, IP addresses of the physician-side adapter 418 and patient-side adapter 426, as described herein). The request to initiate the connection can be transmitted to the connectivity server 434, which can forward a request to begin connection to the physician-side adapter 418. The connectivity server 434 can forward the request to begin connection to the IP address of the physician-side adapter 418. In response to receiving the request to begin connection, the physician-side adapter 418 can generate an offer to connect. The offer can be transmitted to the connectivity server 434, which can forward the offer to the patient-side adapter 426 (for instance, to the IP address of the patient-side adapter 426). The connection can be established responsive to the patient-side adapter 426 receiving the offer.

In some implementations, the network 430 can facilitate server-based connectivity (rather than peer-to-peer connectivity). For example, both adapters 418 and 426 can transmit data packets through the connectivity server 434 to communicate with each other.

In some examples, the system 400 can assess whether a type of a robot 422 is compatible with a physician input console 416. In this example, the system 400 will compare the types of the robot 422 and the physician input console 416 to ensure the types are compatible (such as, the same) prior to providing information to establish a connection between the robot 422 and the physician input console 416. In this example, when the robot 422 is of a first type and the physician input console 416 are of the first type, the system 400 will provide over the network 430 information to one or both of the robot 422 and the physician input console 416 to allow the devices to establish a connection (such as, a peer-to-peer connection) for remotely controlling the robot 422. Such connection can be established between the physician-side adapter 418 and the patient-side adapter 426. In another example, when the robot 422 is of a first type and the physician input console 416 are of a second type that is different from the first type, the system 400 will restrict provision of the information over the network 430 and prevent the devices from establishing the connection.

It should be noted that a preliminary maintenance connection may be formed via the network 430 between a physician-side adapter 418 and a patient-side adapter 426 prior to forming the operational connection for remotely controlling the robot 422. The preliminary maintenance connection can be used by the physician-side adapter 418 and the patient-side adapter 426 for exchanging information related to discovery, status, keeping the preliminary connection alive, or the like. This type of connection can be distinct from an operational connection (where the operational connection may be otherwise known as a "session") for remotely controlling the robot 422 during which the following types of data would be transmitted: control signals (or control commands) transmitted from the physician side to the patient side for moving and/or controlling one or more instruments or imaging systems of a robot 422, status information transmitted from the patient side to the physician side or from the physician side to the patient side (such as, heartbeat signal or other data for ensuring safety), and image data of the procedure site transmitted from the patient side to the physician side. When the operational connection for remotely controlling the robot 422 is established between a physician-side adapter 418 and a patient-side adapter 426, all these three types of data would be exchanged between the physician side and patient side.

Status information can include transmission of signals from the patient side to the physician side and from the physician side to the patient side for monitoring the status of the system 400. For example, the patient side can transmit to the physician side status information indicating that it is operating normally (for instance, this can be a heartbeat signal). As another example, the physician side can transmit to the patient side status information that it is operating normally.

In some instances, a connection for remotely controlling a robot 422 would not be established (and the three types of data described herein would not be exchanged) unless there has been coordination between the patient side and physician side. Coordination can include one or more of performing safety checks (such as, compatibility between the types of the physician input console 416 and the robot 422), ensuring that the patient site (such as, the operating room) and robot 422 have been prepared for a medical procedure, ensuring that the patient has been prepared for the procedure, or the like. In some cases, coordination can be performed by the system 400 and may include completion of or more checklists on the patient side (for instance, by a circulating nurse) and attestation by the physician that the one or more checklists have been completed correctly (such as, by clicking "Attest" on a user interface displayed on the monitor 414). A checklist can be completed on a nurse PC 420, transmitted to the physician side via the network 430, displayed on a physician PC 412, and attested to by the physician through the physician PC 412.

In some instances, at least some types of data related to the connection may be transmitted prior to establishing a connection for remotely controlling a robot 422. For example, image data of the procedure site may be transmitted to help the physician prepare for a procedure (such as, plan the procedure). Transmission of control signals and status information may be commenced at the same time.

A session for remotely controlling the robot 422 can be associated with a time window during which a physician is allowed to remotely control the robot 422 to perform a medical procedure on a patient, subsequent to a completion of coordination (such as, signoffs) as described herein. The time window can correspond to the scheduled time of the medical procedure (such as, to an allotted session time slot). After such time window has opened and over duration of the time window, the operational connection from the physician input console 416 to remotely control the robot 422 may be allowed, subsequent to the completion of coordination, while an operational connection from any other physician input console to remotely control the robot 422 may be disallowed. After the time window has ended, an operational connection from the physician input console 416 to remotely control the robot 422 may be disallowed as it is possible that another time window has been opened to permit the same or another physician input console to connect to the robot 422 to remotely control the robot to perform a medical procedure on a different patient. That is, time windows for remotely controlling a particular robot can be arranged in non-overlapping chronological order. The operational connection may be initiated responsive to completion of the coordination between the patient side and physician side, which, as described herein, can involve completion of one or more checklists and attestation of the one or more checklists (this can be referred to as signoffs). The physician can be informed that the time window has been opened, for instance, via the surgeon PC 412 and the monitor 414 (such as, via a status being shown on a schedule). In response to the notification, the physician can initiate the operational connection to remotely control the robot (for instance, by clicking "Attest" on the user interface displayed on the monitor 414). On the patient side, the clinical staff can be informed that the time windows have been opened, for instance, via the nurse PC 420.

The orchestration application 432 can include an orchestration and collaboration platform for physicians, patients, clinical staff, and administrative personnel to manage remote robotic procedure programs. The orchestration application 432 can be executed on one or more remote servers in the cloud 406 and can be operably connected to the health system information system 408, one or more A/V systems 410, one or more physician PCs 412, one or more nurse PCs 420, connectivity server 434, the adapter management system 436, the data and analytics platform 438, and the network management system 435. In some examples, the orchestration application 432 is configured to assess whether a type of a robot 422 is compatible with a physician input console 416.

The assessment of compatibility can occur prior to or at a time of a procedure. For example, the system 400 (such as, via the orchestration application 432) can assess the compatibility at the time the procedure is scheduled, which can be well before the time of procedure (such as, hours, days, or weeks) and well before the connection for remotely controlling the robot 422 is established between the adapters 418 and 426. As a safety check, compatibility may be verified again prior to forming the connection.

In another example, the system 400 can assess compatibility at the time of procedure (such as, close to the initiation of the connection). This can be performed minutes or even seconds prior to the procedure.

The process for the orchestration application 432 to assess the compatibility between a robot 422 and the physician input console 416 can be an automated process, where there is no user intervention to begin the assessment of the compatibility. For example, the orchestration application 432 can pre-verify compatibility of the types prior to when the connection for remotely controlling the robot 422 is established.

The system 400 (such as, via the orchestration application 432) can compare the types of a robot 422 and a physician input console 416 to ensure the types are compatible prior to establishment of the connection for remotely controlling the robot 422. For example, when the robot 422 is of a first type and the physician input console 416 are of the first type, the orchestration application 432 can provide over the network 430 information to one or both of the patient-side adapter 426 and physician-side adapter 418 to allow the devices to establish a connection (such as, a peer-to-peer connection). In another example, when the robot 422 is of a first type and the physician input console 416 are of a second type that is different from the first type, the orchestration application 432 will restrict provision of the information over the network 430 and prevent the devices from establishing the connection.

The connectivity server 434 can include a network signaling server. The connectivity server 434 can be operably coupled to one or more physician-side adapters 418, one or more patient-side adapters 426, the orchestration application 432, and the data and analytics platform 438. The connectivity server 434 can provide a service of connecting the physician-side adapter 418 and the patient-side adapter 426.

For example, the connectivity server 434 can receive a request from a physician-side adapter 418 to establish a connection with a patient-side adapter 426 (or vice versa). In this example, the connectivity server 434 can obtain the physician-side adapter 418 information, including an identifier, an external IP address (if needed), an internal IP address and patient-side adapter 426 information, including an identifier, an external IP address (if needed), and an internal IP address. The connectivity server 434 can obtain the physician-side adapter 418 information from the physician-side adapter 418 and/or from the adapter management system 436. In this example, the connectivity server 434 can also receive an identifier of the patient-side adapter 426 from the physician-side adapter 418, indicating the patient-side adapter 426 with which to establish a connection. The connectivity server 434 can then transmit a request to the patient-side adapter 426, to determine whether the patient-side adapter 426 is capable of establishing a connection to the physician-side adapter 418 over the network 430. In response to receiving an approval from the patient-side adapter 426, the connectivity server 434 can transmit the patient-side adapter 426 information to the physician-side adapter 418 to allow the physician-side adapter 418 to establish a connection between the adapters (for example, via the network 430). In this example, the connectivity server 434 can transmit the patient-side adapter 426 identifier, internal IP address, and external IP address (if needed). The connectivity server 434 can provide a threshold security procedure to assess whether the physician-side adapter 418 has authorization to establish a connection with the patient-side adapter 426. In this example, the connectivity server 434 can include an access control list of authorized adapters and compare the identifier of the physician-side adapter 418 to verify authorization.

In another example, the connectivity server 434 can receive a request from a patient-side adapter 426 to establish a connection with a physician-side adapter 418. The connectivity server 434 can also obtain the patient-side adapter 426 information, including an identifier, an external IP address (if needed), an internal IP address and patient-side adapter 426 information, including an identifier, an external IP address (if needed), and an internal IP address. The connectivity server 434 can obtain the patient-side adapter 426 information from the patient-side adapter 426 and/or from the adapter management system 436. The connectivity server 434 can also receive an identifier of the physician-side adapter 418 from the patient-side adapter 426, indicating the physician-side adapter 418 with which to establish a connection. The connectivity server 434 can then transmit a request to the physician-side adapter 418, to determine whether the physician-side adapter 418 is capable of establishing a connection to the patient-side adapter 426 over the network 430. In response to receiving an approval from the physician-side adapter 418, the connectivity server 434 can then transmit the physician-side adapter 418 information to the patient-side adapter 426 to allow the patient-side adapter 426 to establish a connection between the adapters (for example, via the network 430). In this example, the connectivity server 434 can transmit the physician-side adapter 418 identifier, internal IP address, and external IP address (if needed). The connectivity server 434 can provide a threshold security procedure to assess whether the patient-side adapter 426 has authorization to establish a connection with the physician-side adapter 418. In this example, the connectivity server 434 can include an access control list of authorized adapters and compare the identifier of the patient-side adapter 426 to verify the authorization.

In another example, the connectivity server 434 can receive a request from the orchestration application 432 to establish a connection between a physician-side adapter 418 and a patient-side adapter 426. The connectivity server 434 can obtain the physician-side adapter 418 information, including an identifier, an external IP address (if needed), an internal IP address and patient-side adapter 426 information, including an identifier, an external IP address (if needed), and an internal IP address. The connectivity server 434 can obtain the information from the adapters and/or from the adapter management system 436. For instance, the connectivity server 434 can receive the patient-side adapter 426 identifier from the orchestration application 432 to establish a connection between the patient-side adapter 426 and the physician-side adapter 418. The connectivity server 434 can then transmit a request to the physician-side adapter 418 to determine whether the physician-side adapter 418 is capable of establishing a connection to the patient-side adapter 426 over the network 430. In response to receiving approval from the physician-side adapter 418, the connectivity server 434 can then transmit the physician-side adapter 418 information to the patient-side adapter 426 to allow the physician-side adapter 418 to establish a connection between the adapters (for example, via the network 430). In this example, the connectivity server 434 can transmit the physician-side adapter 418 identifier, internal IP address, and external IP address (if needed) for the patient-side adapter 426 to establish a connection with the physician-side adapter 418. The connectivity server 434 can provide a threshold security procedure to assess whether the adapters have authorization to establish a connection across the network 430. The connectivity server 434 can include an access control list of authorized adapters and compare the identifiers of the adapters to verify authorization.

The adapter management system 436 can provide adapter monitoring and management. The adapter management system 436 can be operably coupled to one or more physician-side adapters 418, one or more patient-side adapters 426, the orchestration application 432, and the data and analytics platform 438. In an example, the adapter management system 436 can store information regarding adapters connected to the cloud 406. The information stored can include identifiers, internal IP addresses, and external IP addresses (if needed) of the adapters. In this example, the adapters connected to the cloud 406 are in a trusted state (for instance, part of the same SD-WAN), such that the adapter management system 436 communicates directly with the adapters. In this example, the adapter management system 436 can communicate with the adapters as if the adapters are on the same local network, such that there is no need to communicate using an external IP address, as described herein.

The data and analytics platform 438 can include a data repository for analysis and reports, which can improve the performance of the medical procedure teams and technology that facilitates remote robotic-assisted procedures. The data and analytics platform 438 can be operably coupled to the orchestration application 432, the connectivity server 434, the network management system 435 and the adapter management system 436. The data and analytics platform 438 can store data from remote robotic procedures performed using the system 400.

The aforementioned components of the system 400 (such as, one or more of the health system information systems 408, a medical-grade A/V system 410, a physician PC 412, a monitor 414, a physician input console 416, a physician-side adapter 418, a nurse PC 420, a robot 422, an imaging system 424, a patient-side adapter 426, the cloud 406, the orchestration application 432, the connectivity server 434, the network management system 435, the adapter management system 436, connectivity clients 415 or 425, gateways 419 or 429, or the data and analytics platform 438) can be communicably coupled to each other via the network 430 and/or the cloud 406, such that data can be transmitted between the components. The network 430 and the cloud 406 can include the Internet, intranet, or other suitable network. The data transmission can be encrypted, unencrypted, over a virtual private network (VPN) tunnel, or other suitable communication means. The network 430 and the cloud 406 can be a wide area network (WAN) (such as, SD-WAN), local area network (LAN), personal area network (PAN), or another suitable network type. The network communication between any of the system 400 components can be encrypted using pretty good privacy (PGP), Blowfish, Twofish, triple data encryption standard (3DES), hypertext transfer protocol secure (HTTPS), or other suitable encryption. The system 400 can be configured to provide communication via the various systems, components, and modules disclosed herein via an application programming interface (API), peripheral component interface (PCI), PCI-Express, American National Standards Institute (ANSI)-X12, Ethernet, Wi-Fi, Bluetooth, or other suitable communication protocol or medium. Additionally, third party systems and databases can be operably coupled to the system components via the network 430 and/or the cloud 406. For example, an EHR/EMR system (such as, the system 408) can be operably coupled to the cloud 406 to transmit patient information, scheduling information relating to a procedure, physician information, or any other relevant information to perform remote robotic procedure.

The data transmitted to and from the components of system 400, can include any format, including JavaScript Object Notation (JSON), transfer control protocol (TCP)/IP, extensible markup language (XML), hypertext markup language (HTML), American Standard Code for Information Interchange (ASCII), short message service (SMS), comma-separated value (CSV), representational state transfer (REST), or other suitable format. The data transmission can include a message, flag, header, header properties, metadata, and/or a body, or be encapsulated and packetized by any suitable format having same.

The network 430 and/or the cloud 406, including the orchestration application 432, connectivity server 434, network management system 435, adapter management system 436, and data and analytics platform 438, can be implemented in hardware, software, or a suitable combination of hardware and software therefor, and may comprise one or more software systems operating on one or more servers having one or more processors with access to memory. The network 430 and/or the cloud 406, including the orchestration application 432, connectivity server 434, network management system 435 adapter management system 436, and data and analytics platform 438, can include electronic storage, one or more processors, and/or other components. The network 430 and/or the cloud 406, including the orchestration application 432, connectivity server 434, network management system 435 adapter management system 436, and data and analytics platform 438, can include communication lines, connections, and/or ports to enable the exchange of information via a network 430 and/or the cloud 406, and/or other computing platforms. The network 430 and/or the cloud 406, including the orchestration application 432, connectivity server 434, network management system 435 adapter management system 436, and data and analytics platform 438, can also include a plurality of hardware, software, and/or firmware components operating together to provide the functionality attributed herein. For example, the network 430 can be implemented by a cloud of computing platforms operating together as the network 430, including Software-as-a-Service (SaaS) and Platform-as-a-Service (PaaS) functionality. Additionally, the cloud 406 can be implemented using commercial cloud computing platforms, including all such functionality provided by the commercial cloud computing platform.

Any of the components of the system 400 can comprise electronic storage that stores information. The electronic storage can include one or both of system storage that can be provided integrally (such as, substantially non-removable) with the network 430 and/or the cloud 406, and/or removable storage that can be removably connectable to the network 430 and/or the cloud 406 via, for example, a port (such as, a Universal Serial Bus (USB) port, a firewire port, etc.) or a drive (such as, a disk drive, etc.). Electronic storage may include one or more of optically readable storage media (such as, optical disks, etc.), magnetically readable storage media (such as, magnetic tape, magnetic hard drive, floppy drive, etc.), electrical charge-based storage media (such as, erasable electronic programmable read only memory (EEPROM), random access memory (RAM), etc.), solid-state storage media (such as, flash drive, etc.), and/or other electronically readable storage media. Electronic storage may include one or more virtual storage resources (such as, cloud storage, a virtual private network, and/or other virtual storage resources). The electronic storage can include a database, or public or private distributed ledger (such as, blockchain). Electronic storage can store machine-readable instructions, software algorithms, control logic, data generated by processor(s), data received from server(s), data received from computing platform(s), and/or other data that can enable server(s) to function as described herein. The electronic storage can also include third-party databases accessible via the network 430 and/or the cloud 406.

Any of the components of the system 400 can include control circuitry, such as processor(s) or controller(s), configured to provide data processing capabilities, for instance, in the network 430 and/or the cloud 406. As such, any of the processors can include one or more of a digital processor, an analog processor, a digital circuit designed to process information, an analog circuit designed to process information, a state machine, and/or other mechanisms for electronically processing information, such as field programmable gate arrays (FPGAs) or application specific integrated circuits (ASICs). The processor(s) can be a single entity or include a plurality of processing units. These processing units can be physically located within the same device, or processor(s) can represent processing functionality of a plurality of devices or software functionality operating alone, or in concert. A networked computer processor can be a processor operably coupled to the network 430 and/or the cloud 406. The networked computer processor can be operably coupled to other processors, databases, or components.

The orchestration application 432, connectivity server 434, network management system 435 adapter management system 436, and data and analytics platform 438 can be configured with machine-readable instructions having one or more functional modules. The machine-readable instructions can be implemented on one or more servers, having one or more processors, with access to memory. The machine-readable instructions can be a single networked node, or a machine cluster, which can include a distributed architecture of a plurality of networked nodes. The machine-readable instructions can include control logic for implementing various functionality, as described in more detail below. The machine-readable instructions can include certain functionality associated with the system 400. Additionally, the machine-readable instructions can include a smart contract or multi-signature contract that can process, read, and write data to the database, distributed ledger, or blockchain.

FIG. 5 illustrates a schematic view of a remote robotic-assisted medical system 500, which can be similar to the system 400. As is described herein, in system 500, the functionality of a physician-side adapter 418 can be implemented in software and/or firmware by an interface 512, and the functionality of a patient-side adapter 426 can be implemented in software and/or firmware by an interface 514. The interface 512 can be executed by one or more processors of the physician console 416, and the interface 514 can be executed by one or more processors of the robot 422. In some instances, the interfaces 512 and 514 can be SDKs. The functionality of a physician-side connectivity client 415 can be similarly implemented by the interface 512, and the functionality of a patient-side connectivity client 425 can be similarly implemented by the interface 514.

A physician console 416 can include a bridge 502 (which can be implemented in software and/or firmware) that connects the interface 512 with one or more of the orchestration application 432, connectivity server 434, network management system 435, or adapter management system 436. As described herein, the physician console can receive image data 520 from the robot 422, provide control signals 530 to the robot, and exchange status information 540 with the robot. In some instances, the bridge 502 can function as or similarly to the gateway 419, which can forward traffic between the interface 512 and one or more of the orchestration application 432, connectivity server 434, network management system 435 or adapter management system 436.

A robot 422 can include a bridge 504 (which can be implemented in software and/or firmware) that connects the interface 514 with one or more of the orchestration application 432, connectivity server 434, network management system 435 or adapter management system 436. As described herein, the robot can provide image data 522 to the physician console 416, receive control signals 532 from the physician console, and exchange status information 542 with the physician console. In some instances, the bridge 504 can function as or similarly to the gateway 429, which can forward traffic between the interface 514 and one or more of the orchestration application 432, connectivity server 434, network management system 435 or adapter management system 436.

Network for Remotely Controlling Robotic Procedures

Interconnecting physician input consoles and robotic systems can involve considerable expense and effort. For instance, suppose that a patient site (such as, a hospital or another suitable site) that houses one or more robots desires to allow such one or more robots to be controlled by one or more remotely located physician input consoles. To reduce transmission delay and guarantee reliability and stability of transmission, a high-quality network connection is required rather than using the public Internet, and therefore the hospital would need to design and deploy a suitable network (such as, the network 430) that provides one or more connections between the one or more robots and consoles. A physician site (such as, a medical center, physician center, or another suitable site) housing one or more physician input consoles may need to undergo a similar process. Undesirably, such undertaking can be difficult, time consuming, and expensive. Further, each hospital and physician center that wishes to provide remotely controlled robotic procedures may need to design and deploy its own network, which can lead to wasteful duplication of effort and resources.

To address these shortcomings, a network for remotely controlling robotic procedures can be designed and deployed. Such network can include one or more nodes for connecting patient sites and physician sites. A node can be referred to as a point-of-presence (POP) node (which can also be referred to as a data center). To connect to the network, patient sites and physician sites may only need to employ a suitable last mile or last kilometer connection (sometimes referred to as an onramp connection or onramp) that satisfies network requirements for remote robotic procedures (which are described herein). Last mile connection can connect a patient-side gateway or physician-side gateway to a PoP. For example, a patient site or physician site may utilize a dedicated connection (such as, a leased line) for connecting with a PoP. In some cases, an onramp connection can be a direct connection. A direct connection may not pass through any routers or switches to connect a gateway to a PoP. A direct connection can provide high performance (such as, high bandwidth, low latency, low packet loss, and low jitter). In some cases, an onramp connection can be a fiberoptic connection. The network can be a single network covering a particular geographical area or region (for instance, the continental United States or other regions). Advantageously, this approach can simplify and streamline deployment of remotely-controlled robotic systems.

Figure 6:
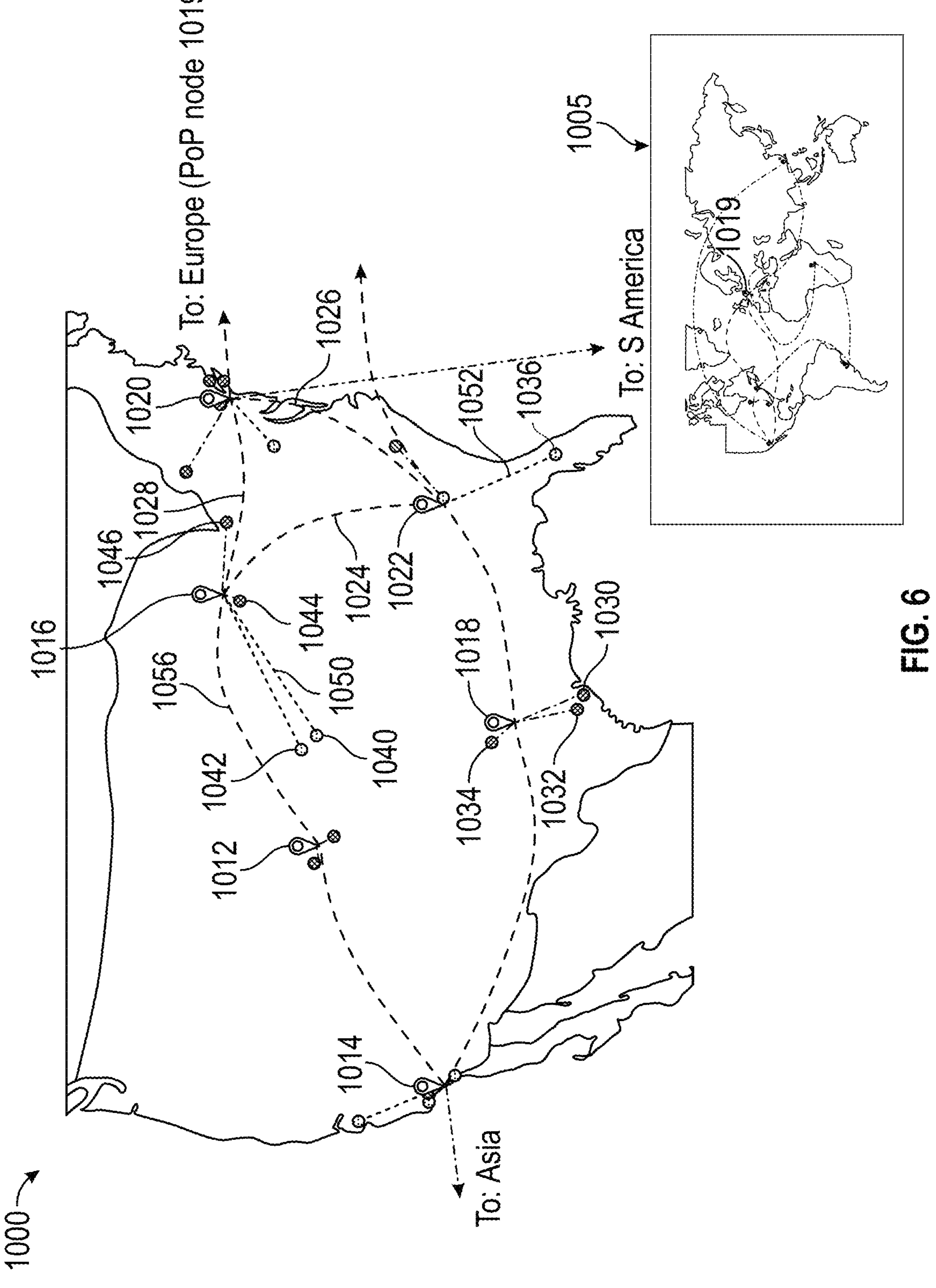
FIG. 6 is a schematic view of a network for remotely controlling robotic surgery.

FIG. 6 illustrates a network 1000 for remotely controlling robotic procedures. The network 1000 is illustrated as covering the continental United States. Another network 1005 is illustrated as covering the continental United States, Canada, Europe, Asia, and Africa. The network 1000 can be a subset of the network 1005. The network 1000 can be a global wide area network (WAN). The network 1000 can include a plurality of POP nodes 1012, 1014, 1016, 1018, 1020, and 1022, and the network 1005 can include at least a PoP node 1019. The POP nodes can serve as regional hubs for connecting patient sites and physician sites. For instance, a plurality of sites 1040 and 1042 each of which houses one or more robotic systems (which can be similar to the robot 422) and a plurality of sites 1044 and 1046 each of which houses one or more physician input consoles (which can be similar to the physician input consoles 416) can utilize the POP node 1016 for connecting to the network 1000. At the same time, a plurality of sites 1030 and 1032 each of which houses one or more physician input consoles and a patient site 1034 that houses one or more robotic systems can utilize the POP node 1018 for connecting to the network 1000. As is described herein, the sites 1030, 1032, and 1034 can each be connected to the POP node 1018 via a suitable last mile connection, and the sites 1040, 1042, 1044, and 1046 can each be connected to the POP node 1016 via a suitable last mile connection. For example, a last mile connection 1050 connects the site 1040 to the POP node 1016.

The network 1000 can guarantee that a physician input console located anywhere in an area, country, or region covered by the network can connect (provided that all other conditions described herein are satisfied) to a robotic system located in another part of the area, country, or region covered by the network. To achieve this, a POP node of the network 1000 can be connected to at least one other PoP node. Some POP nodes can be connected to multiple other PoP nodes, which can provide fallback allocation, failover, and redundancy. PoP nodes can be connected to one another by a backbone connection (or backbone network), such as, 1024, 1026, 1028, or 1056. A backbone connection can be a high-speed direct connection or a high-speed dedicated connection. A dedicated connection can be an exclusive connection that ensures consistent bandwidth and service quality (or, more generally, consistent performance). As described herein, a direct connection may not pass through any routers or switches and can provide high performance (such as, high bandwidth, low latency, low packet loss, and low jitter).

A POP node may be implemented as one or more servers, such as (such as, one or more servers housed in a data center) or can be implemented as software and/or firmware being executed by one or more processors, such as one or more processors of server(s). A data center can house one or more firewalls and one or more network switches (such as, fiberoptic network switches).

Suppose that a physician operating a physician console located at a site 1036 wishes to perform a remote robotic procedure on a patient using a robot located at the site 1040. A connection between the physician console and robot can span or traverse a last mile connection 1052 connecting the site 1036 to the POP node 1022, the backbone connection 1024 between POP nodes 1022 and 1016, and the last mile connection 1050 connecting the POP node 1016 to the site 1040.

As described herein, the network 1000 can be an SD-WAN.

In some instances, any physician console or robot being added to the network would need to be authenticated before joining the network. Authentication can be performed using a digital certificate mechanism, such as a mechanism like that of the 802.1X protocol. For instance, a network server (such as, the connectivity server 434 or the NCS 435) can issue digital certificates that are provided to authorized physician consoles and robots and are used to join the network. When joining the network, a physician console or robot can present its digital certificate to prove its identity, and the digital certificate is validated by the server. Access to the network is granted only if the digital certificate is successfully validated. Each physician console and robot can be assigned a unique digital certificate.

Management of Remote-Controlled Robotic Procedure Systems

For reliability, effectiveness, and safety of remotely controlled robotic procedures, a management system can be configured to review and, if applicable, modify the status, location, type, or other information pertaining to the robots and consoles deployed in a network (such as, the network 1000). In an expansive network, robots and consoles from multiple distinct robotic system manufacturers may be used in multiple facilities operated by multiple distinct health systems (such as, hospitals or physician centers). For example, a robotic system manufacturer that provides multiple robots and consoles for multiple health systems may not be able to quickly identify a malfunctioning robot or console without individually reviewing the status of each robot or console in each health system. Similarly, a robotic system manufacturer may not want other robotic system manufacturers operating within the same network to be able to view information regarding its robots or consoles. As another example, an administrator for a particular health system may not have authorization to access information for robots or consoles patients located at a different healthcare facility managed by another health system.

To address these challenges, an access monitoring management system (sometimes referred to as AMMS) can be designed and deployed. Such system can support distinct groups of users for accessing various information related to the robots and consoles as well as making various changes to the robots and consoles. For example, AMMS can support three levels of users: a network administrator ("super-user"), a health system administrator, and a robotic system manufacturer. To connect to the AMMS, a requesting user may submit a request with the authorization credentials. AMS can grant access to specific robots or consoles depending on the user's authorization level. For example, robotic system manufacturer A can be granted access to all robots and consoles made by the robotic system manufacturer A. As another example, an administrator of health system A can be granted access to all robots and consoles managed by health system A regardless of the manufacturer. As yet another example, a network administrator can be granted access to all robots and consoles on the network regardless of the manufacturer or health system. In some instances, there are multiple network administrators able to access subsets of robots and consoles. For example, there can be a first network administrator that can access all robots and consoles in a first geographic region and a second network administrator that can access all robots and consoles in a second geographic region. The first network administrator may not be able access any robots or consoles in the second geographic region, and the second network administrator may not be able to access any robots or consoles in the first geographic region. Similar approach can be applied to the privileges of one or more of a health system administrator or a robotic system manufacturer. Advantageously, this approach can simplify and streamline the management of remotely controlled robotic systems.

A first set of robots and consoles that can be accessed by a robotic system manufacturer can overlap, but be different that a second set of robots or consoles that can be accessed by a health system administrator. For instance, a robotic system manufacturer A is able to access some robots in Hospital C and other robots in Hospital D, but not all robots in either Hospital C or Hospital D, which also have robots manufactured by robotic system manufacturer B.

AMMS can be implemented by one or more computers, such as one or more servers.

Figure 7A:
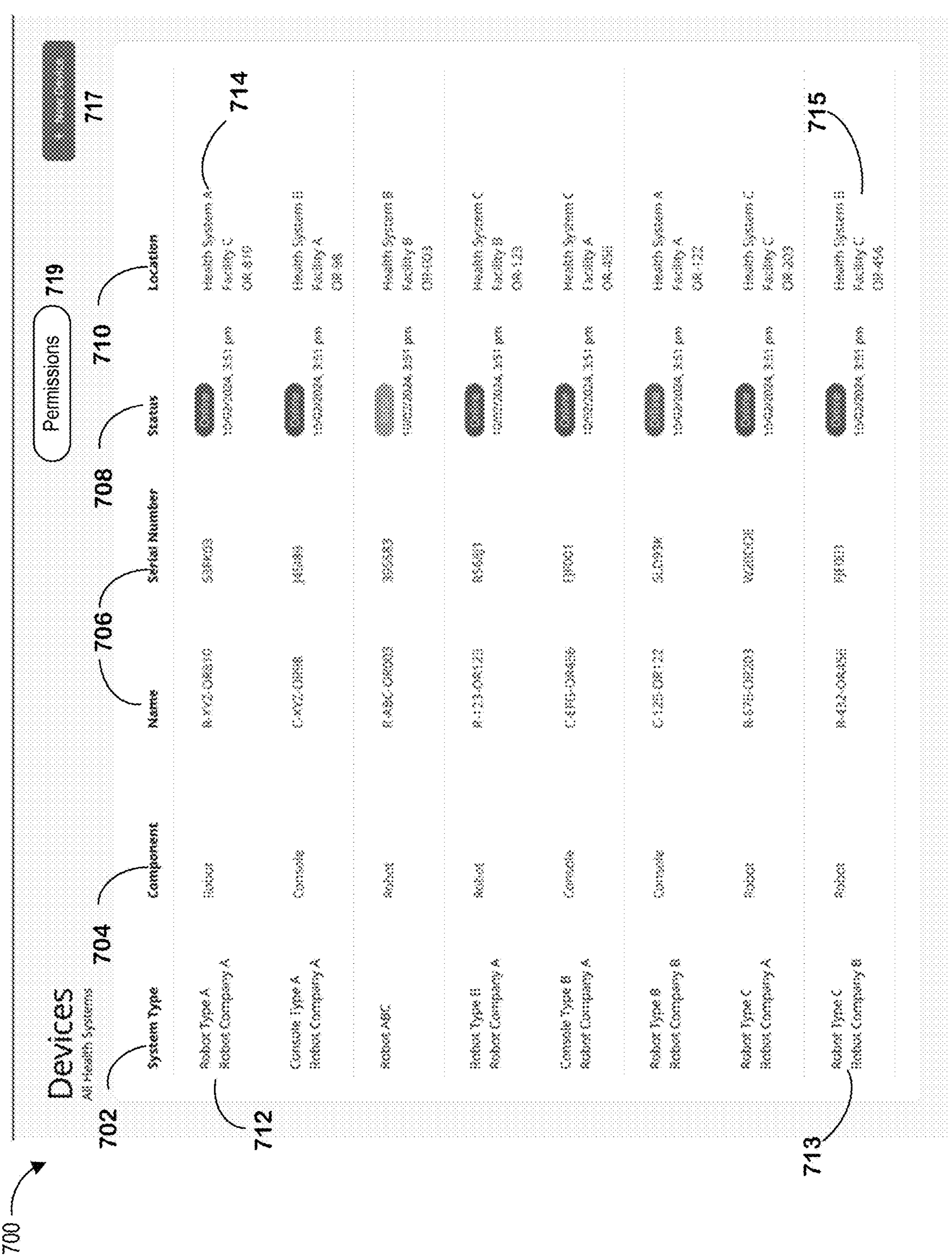
FIGS. 7A-7E are illustrative views of user interfaces provided to various users of various access levels.

FIG. 7A illustrates a user interface 700 presented by AMMS to the network administrator. The user interface 700 provides management information for all robots and consoles within a network (such as, the network 1000). The user interface 700 can provide device information including one or more of a device type 702, a device component type 704, device identifiers 706, a device status 708, and a device location 710. As is illustrated, the network administrator is presented with information for all robots and consoles on the network regardless of the manufacturer or health system.

The device type 702 may include the robot/console type and the robotic system manufacturer name. For example, a first robot 712 is of type A and manufactured by Company A, whereas a second robot 713 is of type C and manufactured by Company B.

The device component type 704 can specify whether the device is a robot or a console. The network administrator can access different data from the device depending on whether it is a robot or a console. For example, following an action by the physician on the physician input console 416, the network administrator can access control data generated by the console or response data transmitted by a robot 422 to the console, which can be helpful for troubleshooting. As another example, the network administrator can access image data transmitted by the robot 422 to the console, which can be helpful for troubleshooting.

The device identifiers 706 can include name and serial number. The device identifiers 706 may be used to identify the make and model of the device. In some cases, the device identifiers 706 may be used to link the devices to other instances of the device in one or more separate databases.

The device status 708 may include the status of the device in the network 1000. The device status 708 may indicate that the device is "Online" (such as, working as intended), "Error" (such as, the device is connected to the network but is malfunctioning), or "Offline" (such as, the device is no longer connected to the network). The device status 708 could be used by a user from each access level (such as, network administrator, robotic system manufacturer, or health system administrator) to quickly locate a faulty device in the network. The device status 708 may also include date and time on which the device last sent a status report. For example, a device with "Offline" device status may have sent the last status report three hours earlier than a device with an "Online" device status. This may indicate to the user that the device has been disconnected from the network for at least three hours and needs attention. Indications of device status 708 can be shown in different color or otherwise depicted differently for user's convenience. For instance, "Error" and "Offline" can each be shown in a different color than "Online"

Figure 8A:
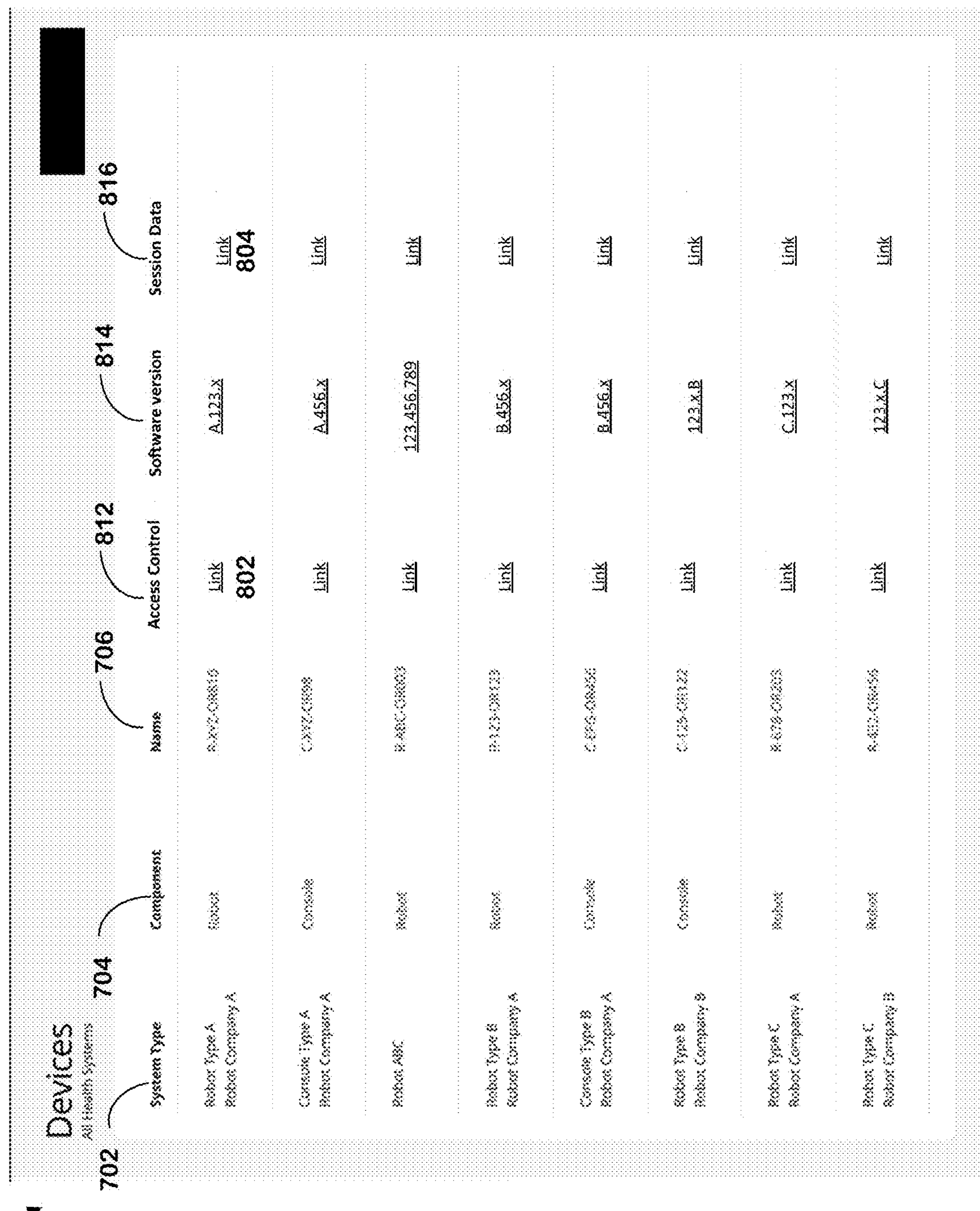
FIGS. 8-10 are illustrative views of user interfaces for modifying physician access.

In addition to viewing the device status, control view of the device can be provided by selecting "Permissions" control 719 (see, for example, FIG. 8A). As described herein, control of the device can include upgrading firmware or software, making other changes to device hardware, modifying device access by a physician or operating room staff, providing various data during remote medical procedure, among others. Control view can be used for management, monitoring, and troubleshooting.

The device location 710 may include the physical location of the device. The device location 710 may include the health system, the specific facility within the health system, and the room number within the facility in which the device is located. For example, Health System A may include one or more facilities. Likewise, each facility may include one or more operating rooms. It may be time consuming and difficult to locate a device when a health system has multiple facilities with multiple operating rooms. In such cases, AMMS allows to quickly locate the device.

As described herein, in the illustrated example of FIG. 7A, the requesting user is the network administrator. The network administrator can obtain access various health systems throughout the network 1000. The network administrator has access to management information for all devices (irrespective of manufacturers) located at all health systems within the network 1000. For example, the network administrator can access management information for the first robot 712 manufactured by Company A operated by a Health System A 714 and management information for the second robot 713 manufactured by Company B operated by Health System B 715.

The network administrator can check device status, view data generated during remote medical procedure, troubleshoot any of the devices, upgrade firmware or software, or make other changes to device hardware, among others. The network administrator may access and manage controls for the devices, such as add or modify which physicians can access which robots, control which firmware or software version the device operates on (for instance, update or modify the firmware or software version or make other changes to device hardware), or access control data, image data, log data, A/V data, or any other data generated during a remote medical procedure. The network administrator can add devices to the network via control 717.

Figure 7B:
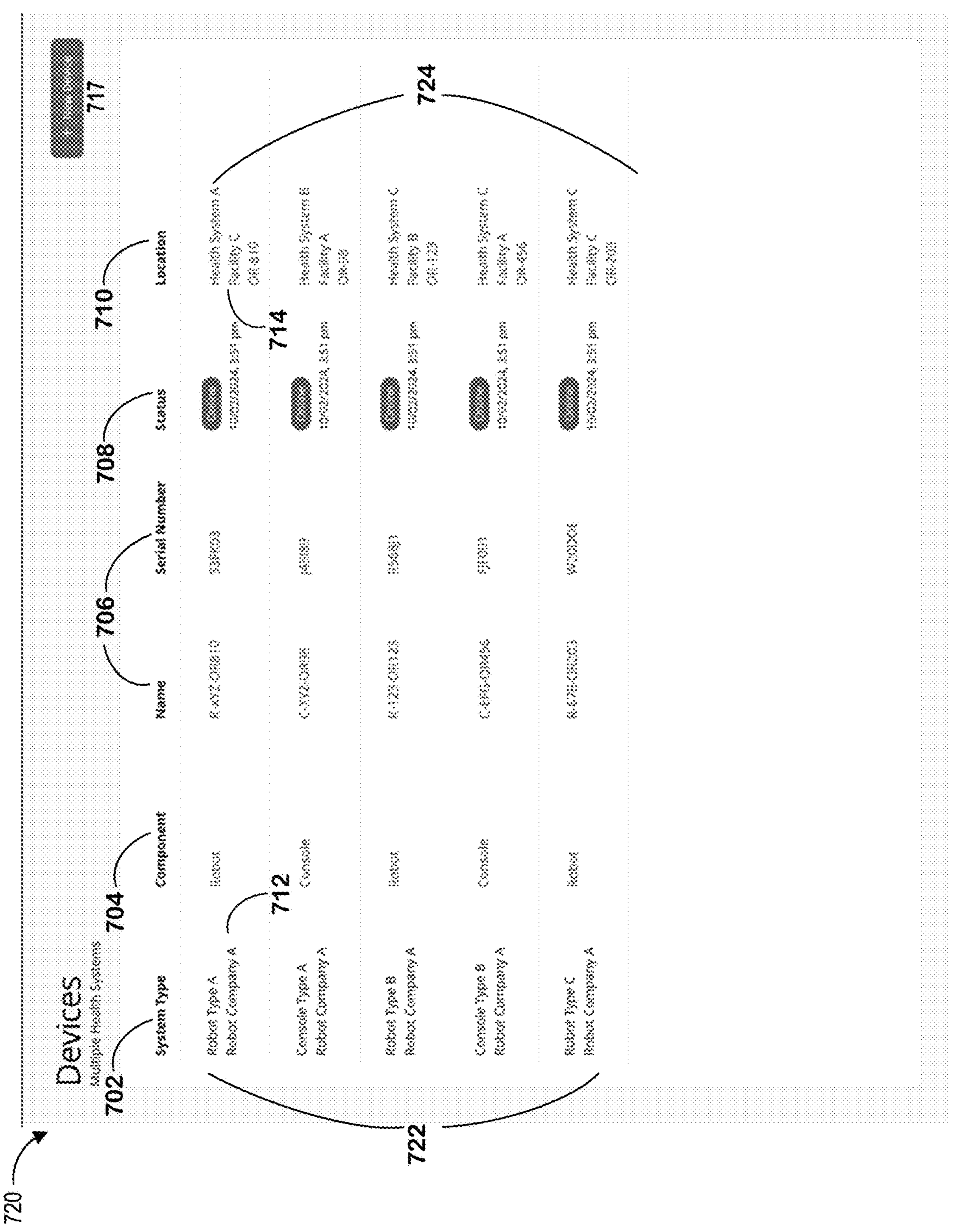

In a further example, the requesting user may be a representative of a robotic system manufacturer company, such as Company A (see the first robot 712). FIG. 7B illustrates an example user interface 720 provided by AMMS for such user. In the example illustrated in FIG. 7B, the user interface 720 includes the device type 702, the device component type 704, the device identifiers 706, the device status 708, and the device location 710, as described herein. The user interface 720 further includes the first robot 712 and the first health system 714, as described herein.

The user interface 720 can be similar to the user interface 700, except that the robotic system Company A representative (such as, an administrator) is provided access to a plurality of devices 722 that were manufactured by Company A. The devices 722 are managed by a plurality of health systems 724. For example, Company A representative is granted access to management information for the first robot 712, as it is manufactured by Company A. However, unlike the network administrator from the example in FIG. 7A, Company A representative is not granted access to the management information for the second robot 713, which is manufactured by Company B. AMMS allows Company A representative to only administer the specific devices manufactured by Company A.

Robotic system manufacturer representative can have authorization to administer specific hardware manufactured by the manufacturer, such as update or modify firmware or software or make other changes to device hardware. Robotic system manufacturer representative may not have authorization to make changes beyond the scope of the representative's authorization level. For example, unlike a network administrator or health system representative, a robotic system manufacturer representative would not have authorization to change access permissions for a physician to control a robot.

As is illustrated, Company A representative has access to management information for devices irrespective of the health system. This specific authorization level allows for a robotic system manufacturer A to efficiently administer their devices operating within the network. Robotic system manufacturer representative can add devices to the network via control 717.

In some cases, the authorization level of the robotic system manufacturer A user may be further refined, such as by using sub-groups. For example, a first Company A representative may only have authorization to access management information for type "A" robots, whereas a second Company A representative may only have authorization to access management information for type "B" robots.

Figure 7C:
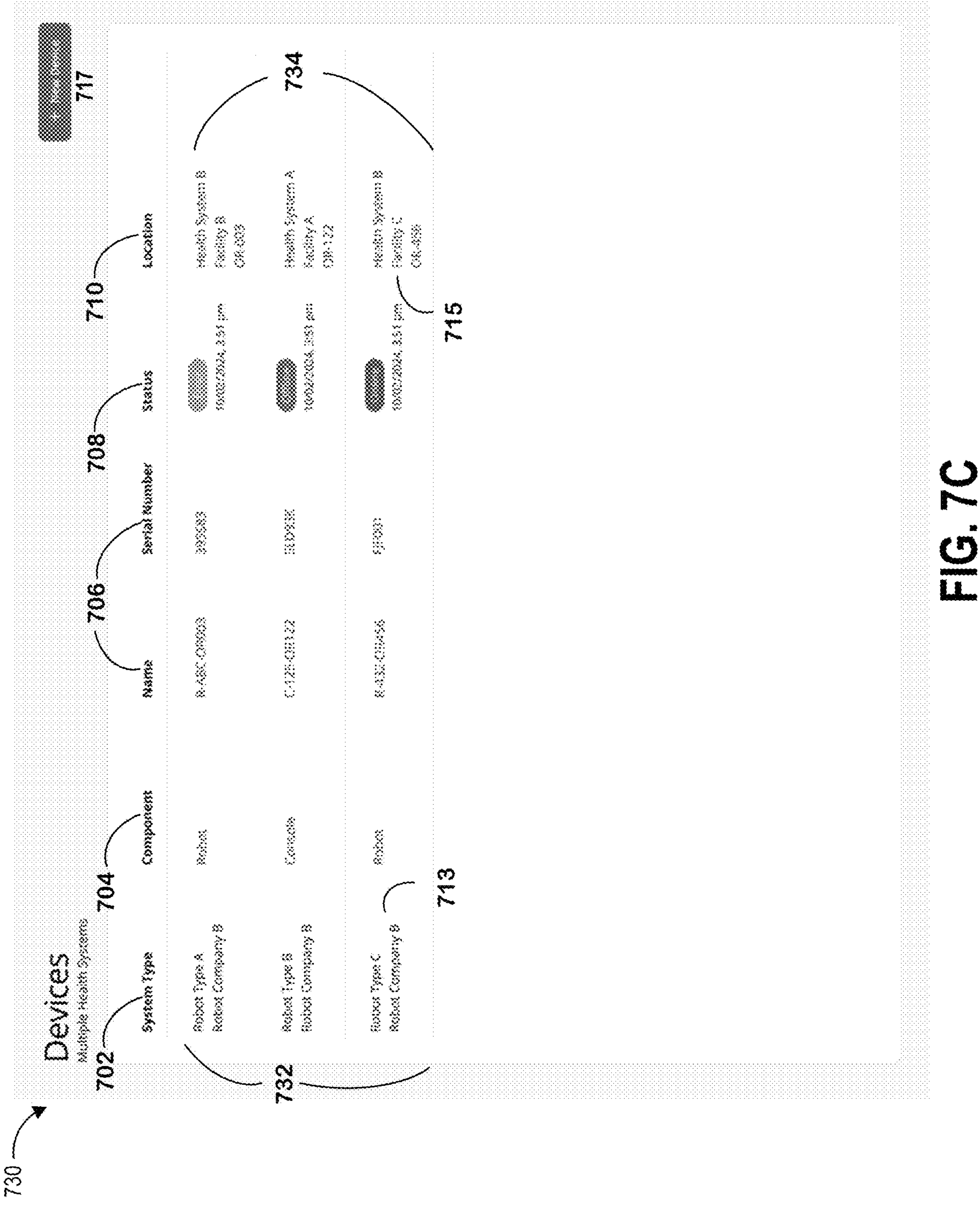

FIG. 7C illustrates an example user interface 730 for a Company B representative. In the example illustrated in FIG. 7C, the user interface 730 includes the device type 702, the device component type 704, the device identifiers 706, the device status 708, and the device location 710, as described herein. The user interface 720 further illustrates the second robot 713 and the Health System B 715, as described herein.

The user interface 730 can be similar to the user interface 720, except Company B representative is granted access to management information for a plurality of robot company B devices 732 managed by a plurality of health systems 734. For example, Company B representative is granted access to the management information for the second robot 713, as it is manufactured by Company B. However, unlike Company A representative illustrated in FIG. 7B, representative of Company B is not able to view the management information for the first robot 712.

Figure 7D:
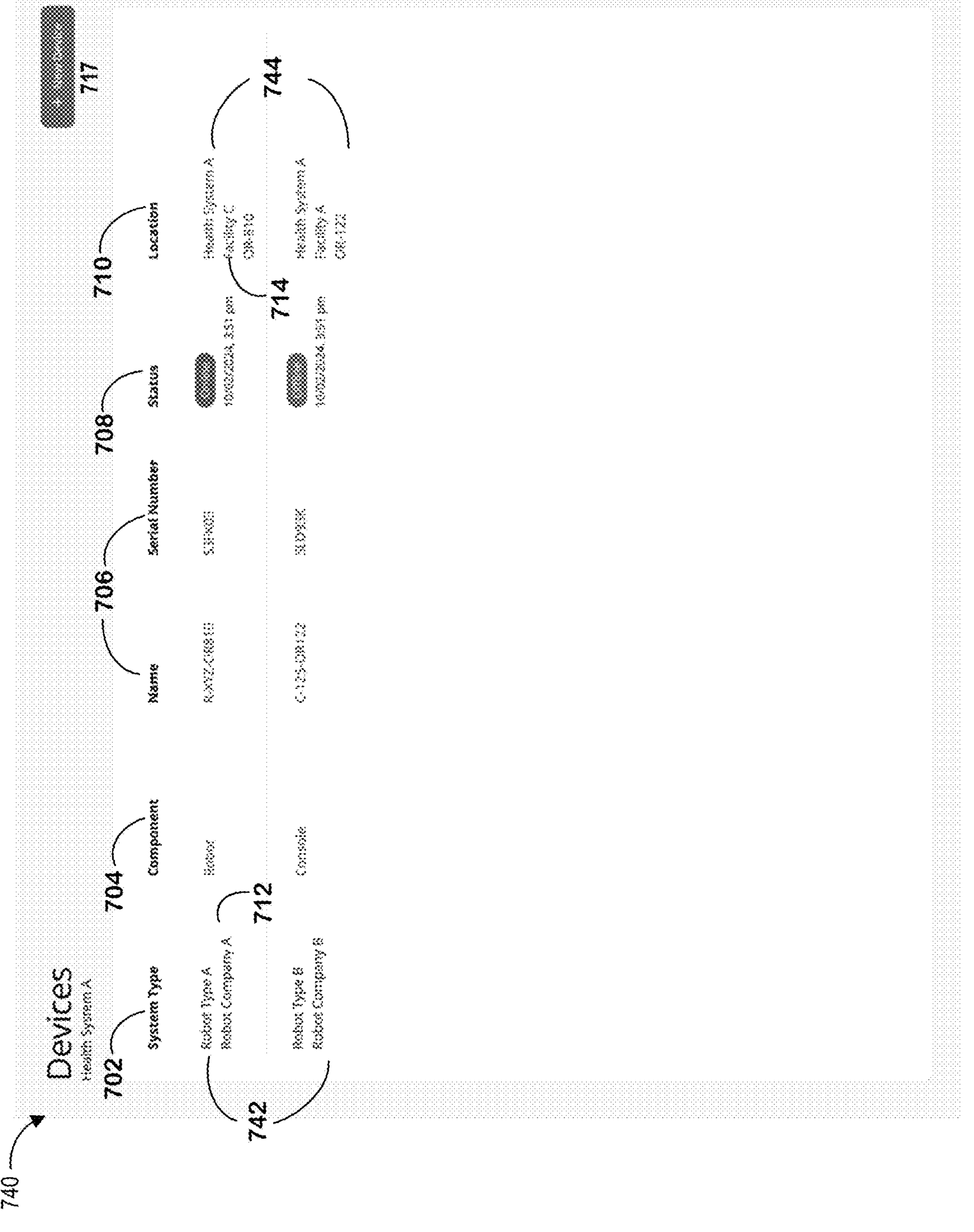

FIG. 7D illustrates an example user interface 740 provided to Health System A representative (such as, administrator). In the example illustrated in FIG. 7D, the user interface 740 includes the device type 702, the device component type 704, the device identifiers 706, the device status 708, and the device location 710, as described herein.

The user interface 740 can be similar to the user interface 700, except that the Health System A representative is only granted access to a plurality of devices 742 managed by Health System A 744. For example, Health System A representative is granted access to the management information for the first robot 712, as it is managed by Health System A, but not the example robot 713, as it is managed by Health System B. By allowing Health System A representative access only to devices managed by Health System A, AMMS promotes information privacy and security among the health systems within the network. Health system administrator can add devices to the network via control 717.

Health system representative can have authorization to only manage the devices managed by the health system, such as update or modify firmware or software, update or modify physician access (for instance, to one or more consoles or robots), or the like, even for devices that are made by different manufacturers. In some cases, a health system representative may not have authorization to update or modify the firmware or software or make other changes to the device hardware.

In some cases, the authorization level of Health System A representative may be further refined, such as by using sub-groups. For example, a first representative from Health System A may only have authorization to access devices in facility "A" within Health System A, whereas a second representative from Health System A may only have authorization to access devices in facility "B" within Health System A.

Figure 7E:
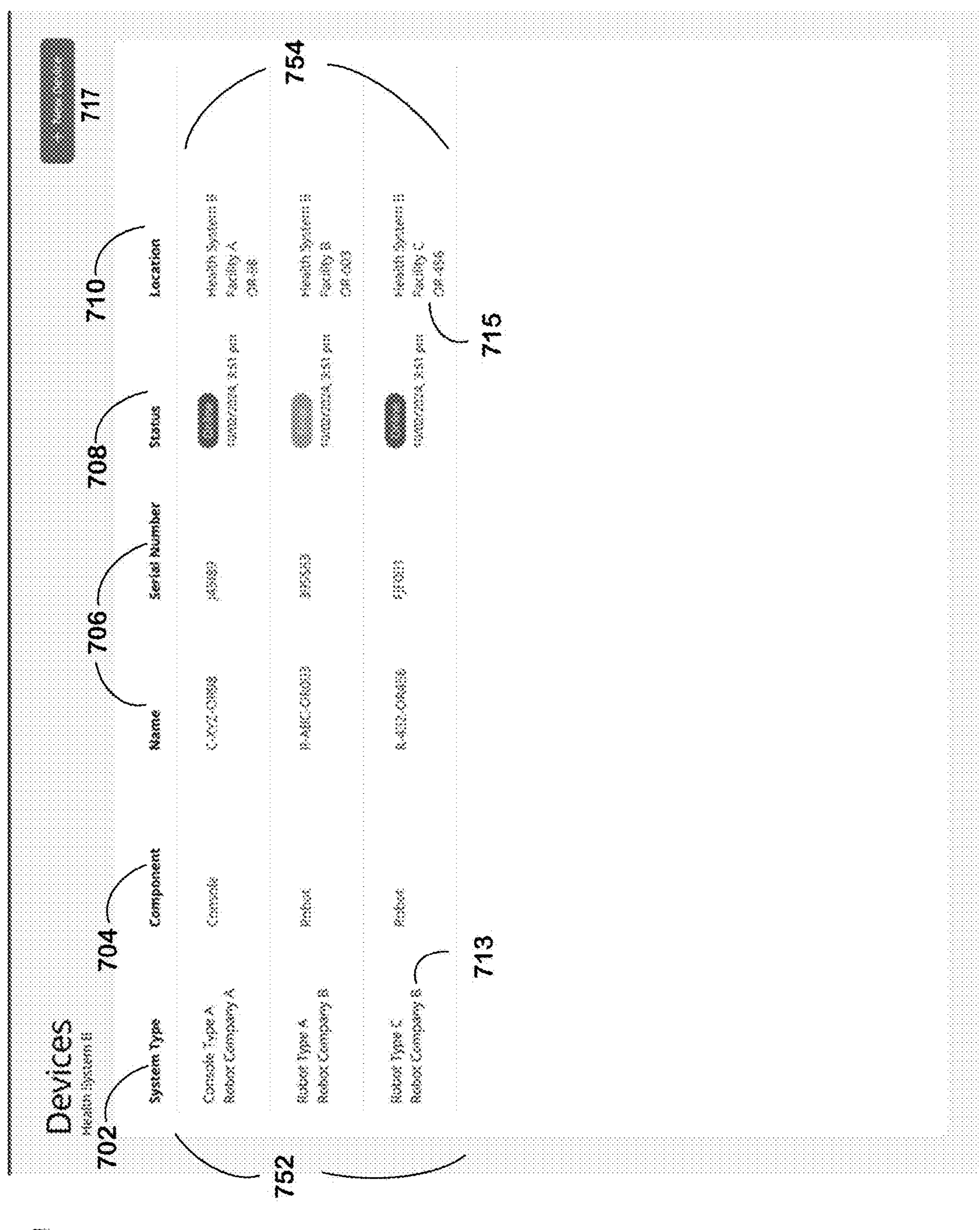

FIG. 7E illustrates an example user interface 750 for a Health System B representative (such as, administrator). In the example illustrated in FIG. 7E, the user interface 750 includes the device type 702, the device component type 704, the device identifiers 706, the device status 708, and the device location 710, as described herein. The user interface 720 further illustrates the second robot 713 and Health System B 715, as described herein.

The user interface 750 can be similar to the user interface 740, except Health System B representative is granted access only to a plurality of devices 752 managed by Health System B 754. For example, Health System B representative is granted access to the second robot 713, as it is managed by Health System B (in facility C), but not the first robot 712.

Health System B representative may have a similar authorization level as Health System A representative. For example, Health System B representative may only have authorization to manage devices within their health system.

As described herein, control of one or more devices can be implemented. Control can include upgrading firmware or software, making other changes to device hardware, modifying device access by a physician or operating room staff, providing various data during remote medical procedure, among others. Control view can be used for management, monitoring, and troubleshooting.

FIG. 8A illustrates an example user interface 800 for management and control. The user interface 800 can be similar to the user interface 700 of FIG. 7A except that modification of one or more of access control 812 and firmware or software version is facilitated and access to session data 816 is provided. The user interface 800 can be presented by AMMS to the network administrator and can list all robots and consoles, as described herein. The user interface 800 can be brought up, for instance, by selecting a control in the user interface 700 (such as, "Permissions" 719).

Access control 812 can facilitate changing physician access. Entries in this list can provide links (such as, a hyperlink 802) to bring up a separate access control user interface 830 illustrated in FIG. 8B for modifying physician access. Entries in the firmware/software update list 814 can be selected (such as, clicked) to update the firmware/software version. This can be facilitated by uploading a file with update version or an optional separate interface displaying all available versions. In some instances, a link or another control (such as, button) can be provided in the firmware/software update list 814 to bring up a separate user interface for modifying firmware/software. Entries in session data 816 list can provide links (such as, a hyperlink 804) to bring up a separate session data user interface 850 illustrated in FIG. 8C.

Access control user interface 830 in FIG. 8B can provide a list 832 that includes name(s) of allowed individual physician(s) or allowed physician group(s) for controlling a particular robot or console. As explained herein, for instance in connection with FIG. 9A, a physician group can correspond, for instance, to those physicians who operate in the same hospital. Physician group can be is a hyperlink and can be viewed and updated. Delete action 834 can be provided to remove physician access for a particular physician or physician group. Access period action 836 can be provided to select type of access. For example, one option can be "always" or a time period delineated by start and end date/time for access (see FIG. 9B). For the latter option, access period action 836 can include a link clicking on which would bring up a date/time picker to edit the period. Control 840 (such as, button) can facilitate adding new access permission, such as, adding new physician or physician group.

Session data user interface 850 can lists every session of a particular console or robot, including, for example, one or more of start time, duration, average bandwidth, latency, packet loss, network jitter, number of instrument commands, time to second stage (e.g. time to port placement complete), and a selection (such as, a link) to display a verbose log of everything.

The user interface 800 presented to a robotic system manufacturer interface can provide access control 812 list as read only. The user interface 800 presented to a health system administrator interface can provide the firmware/software update list 814 as read only.

Figure 9A:
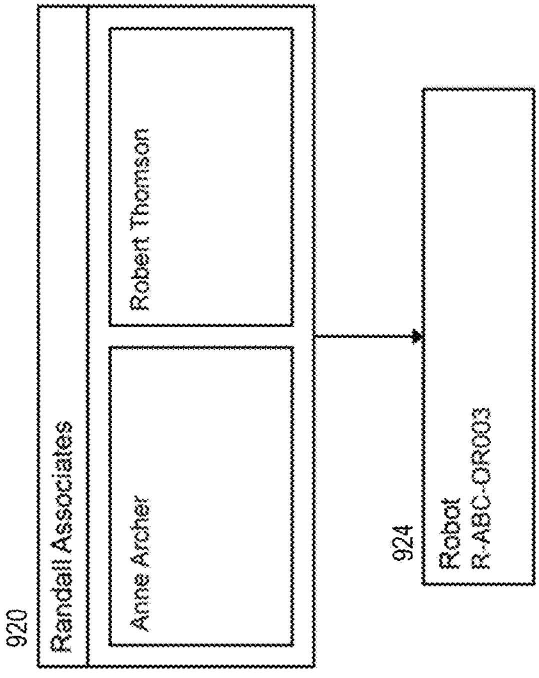
Figure 9A:
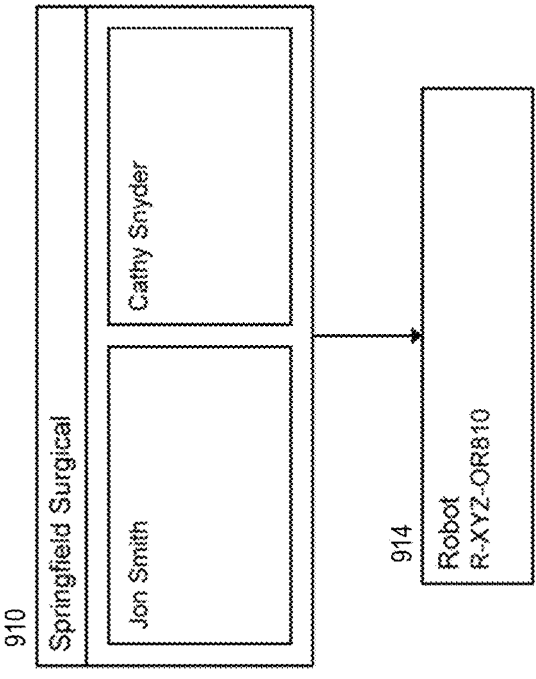

With reference to FIG. 9A, a user interface 900 illustrates assignment of physician to physician groups, for example, by creating rules. For example, user Dr. Jon Smith may be assigned to Springfield Surgical group 910 (along with user Dr. Cathy Snyder), and user Dr. Anne Archer may be assigned Randall Associates group 920 (along with user Dr. Robert Thomson). For safety, it may be important that robots only permit access to physician users who are authorized to perform procedures on those robots. It can be desirable for health system administrators to be able to easily add, modify and delete access, as physician relationships change over time, without having to make requests to network admins each time. It can also be desirable to set permissions based on physician groups, so as not to require each physician permission to be added to each robot, and further to allow simpler and more organized permissions as physicians may join or leave groups over time.

The user interface 900 provides a robot management interface that allows health system administrators (as well as network administrators and, in some cases, robotic system manufacturers) to set physician access permissions.

FIG. 9A shows a desired hierarchy for two robots and two physician groups. Dr. Jon Smith and Dr. Cathy Snyder belong to the Springfield Surgical group 910, and Dr. Anne Archer and Dr. Robert Thomson belong to the Randall Associates group 920. As illustrated, Springfield Surgical group 910 is allowed access to robot 914 (R-XYZ-OR810), and Randall Associates group 920 is allowed access to robot 924 (R-ABC-OR003). These permissions may be set by access permission rules that can be added, deleted or modified, as explained here.

Figure 9B:
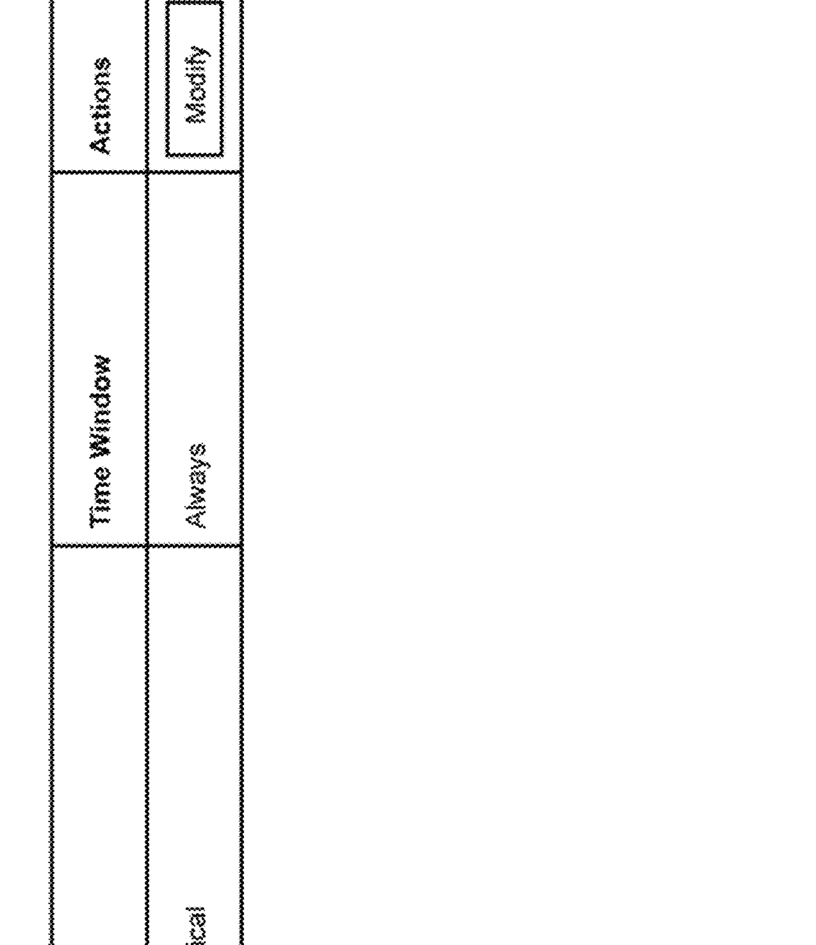

FIG. 9B shows a user interface 950 for changing such access permission rules. The user interface 950 can be accessible to the health system owning robot 914 (R-XYZ-OR810). The user interface 950 can be brought up from the user interface 800. Control 952 (such as, button) can be selected for adding a new access permission rule. For example, as shown in table 954, Springfield Surgical is specified in the "Group or User" column, and "Always" is specified in the "Time Window" column. "Modify" and "Delete" controls (such as, buttons) are shown in "Actions"

column, allowing an existing access permission rule to be edited or removed. A similar user interface 970 shown in FIG. 9C can be accessible to the health system owning robot 924 (R-ABC-OR003).

With these access permission rules in place, for instance, when a request for connection from a physician at a console for controlling robot 914 (R-XYZ-OR810) is received, such connection would be allowed if the user is in the specified group and would be disallowed if the user is not in the specified group.

It can be desirable to allow certain physicians limited-time access to a robot, for example, when they do not belong to a group that normally has access. For example, a specialty surgeon from a different health system may have unique knowledge for a particular patient case and thus may be allowed special-case access for treating that patient.

Figure 10A:
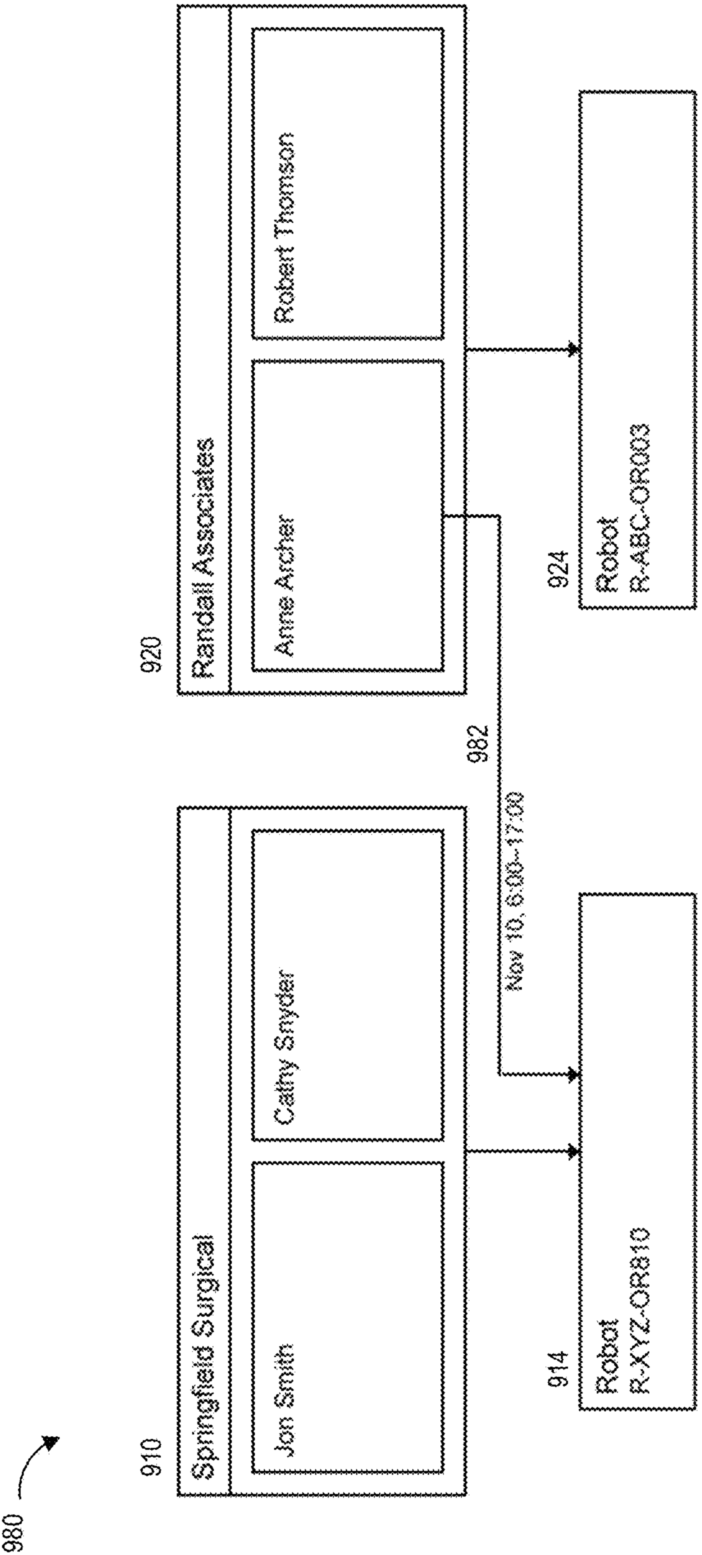

FIG. 10A illustrates a user interface 980 that is a modification of the user interface 900 in FIG. 9A, whereby there is a direct access line 982 drawn from Dr. Anne Archer to robot 914 (R-XYZ-OR810) which is outside her group. Access line 982 is specified as having a specific time window (November 10 6 am-5 μm). FIG. 10B shows a user interface 990, which is similar to the user interface 950 of FIG. 9B, but with an additional entry where there is an entry in table 994 for Dr. Anne Archer along with the specified time window. In this case, when a request for connection from a physician for controlling robot 914 (R-XYZ-OR810) is received, such connection would be allowed if the user is in the Randall Associates group or if the user is Dr. Anne Archer and current time is within the specified time window.

In some implementations, robots can be specified as belonging to a health system. In those cases, a health system-level permission rule can be added applying automatically to access of all robots in that health system, thereby saving time of applying rules to each robot individually. Health system-level rules would be added in a different health system-level interface (not shown). Then, in the robot-level view discussed above, the applicable rule would be displayed in a highlighted color (or with some other distinction), and any attempt to edit or delete would bring up the health-system level interface.

In some instances, option to modify any of the settings (such as, physician access or firmware/software) would be activated by AMMS (for instance, corresponding user interface would be brought up) only if the user had the appropriate authorization level to perform the modification. For instance, the user interface 900 would be displayed only to a health system administrator that has authorization to modify permissions for Springfield Surgical and Randal Associates.

Other Variations

Any of the approaches described herein can utilize any of the examples disclosed in U.S. Pat. Nos. 12,089,906, 12,064,202, U.S. application Ser. No. 19/191,839 filed on Apr. 28, 2025, U.S. application Ser. No. 19/273,503 filed on Jul. 18, 2025, U.S. application Ser. No. 19/273,545 filed on Jul. 18, 2025, U.S. application Ser. No. 19/273,589 filed on Jul. 18, 2025, each of being incorporated by reference in its entirety.

While displaying has been used to describe certain examples of outputting information, any type of visual, auditory, or tactile output can be performed in addition to or alternatively.

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value.

Features, materials, characteristics, or groups described in conjunction with a particular aspect, implementation, or example are to be understood to be applicable to any other aspect, implementation, or example described herein unless incompatible therewith. All of the features disclosed in this specification (including any accompanying claims, abstract and drawings), and/or all of the steps of any method or process so disclosed, can be combined in any combination, except combinations where at least some of such features and/or steps are mutually exclusive. The protection is not restricted to the details of any foregoing implementations. The protection extends to any novel one, or any novel combination, of the features disclosed in this specification (including any accompanying claims, abstract and drawings), or to any novel one, or any novel combination, of the steps of any method or process so disclosed.

While certain implementations have been described, these implementations have been presented by way of example only and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some cases, the actual steps taken in the processes illustrated and/or disclosed may differ from those shown in the figures. Depending on the implementation, certain of the steps described above may be removed, others may be added. For example, the actual steps and/or order of steps taken in the disclosed processes may differ from those shown in the figure. Various components illustrated in the figures or described herein may be implemented as software and/or firmware on a processor, controller, ASIC, FPGA, and/or dedicated hardware. The software or firmware can include instructions stored in a non-transitory computer-readable memory. The instructions can be executed by a processor, controller, ASIC, FPGA, or dedicated hardware. Hardware components, such as controllers, processors, ASICs, FPGAs, and the like, can include logic circuitry. Furthermore, the features and attributes of the specific examples disclosed above may be combined in different ways to form additional implementations, all of which fall within the scope of the present disclosure.

Conditional language used herein, such as, among others, "can," "could", "might," "may," "e.g.," and the like, unless specifically stated otherwise, or otherwise understood within the context as used, is generally intended to convey that certain implementation include, while other implementations do not include, certain features, elements and/or states. Thus, such conditional language is not generally intended to imply that features, elements and/or states are in any way required for one or more implementations or that one or more implementations necessarily include logic for deciding, with or without author input or prompting, whether these features, elements and/or states are included or are to be performed in any particular implementation. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language, such as the phrase "at least one of X, Y and Z," unless specifically stated otherwise, is to be understood with the context as used in general to convey that an item, term, etc. may be either X, Y, or Z, or a combination thereof. Thus, such conjunctive language is not generally intended to imply that certain implementations require at least one of X, at least one of Y and at least one of Z to each be present.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, or within less than 0.01% of the stated value.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations.

While specific implementations have been described and illustrated, such implementations should be considered illustrative only and not as limiting. Accordingly, the scope of the present disclosure is not intended to be limited by the specific disclosures of preferred implementations herein, and may be defined by claims as presented herein or as presented in the future.

EXAMPLE IMPLEMENTATIONS

Examples of the implementations of the present disclosure can be described in view of the following example clauses. The features recited in the below example implementations can be combined with additional features disclosed herein. Furthermore, additional inventive combinations of features are disclosed herein, which are not specifically recited in the below example implementations, and which do not include the same features as the specific implementations below. For sake of brevity, the below example implementations do not identify every inventive aspect of this disclosure. The below example implementations are not intended to identify key features or essential features of any subject matter described herein. Any of the example clauses below, or any features of the example clauses, can be combined with any one or more other example clauses, or features of the example clauses or other features of the present disclosure.

Clause 1. A system for remotely controlling robotic medical procedures, the system including: a plurality of physician consoles, each physician console configured to: transmit control data to a patient-side robotic procedure system of a plurality of patient-side robotic procedure systems to cause the patient-side robotic procedure system to control one or more of at least one instrument or at least one imaging system, the plurality of physician consoles located remotely from the plurality of patient-side robotic procedure systems, the plurality of patient-side robotic procedure systems, each robotic procedure system configured to: receive control data and use the control data to control one or more of at least one instrument or at least one imaging system; and transmit image data obtained by the at least one imaging system to a physician console, wherein the plurality of physician consoles and the plurality of patient-side robotic procedure systems include physician consoles and robotic procedures systems of different manufacturer types and being administered by different entities; and at least one non-transitory computer readable medium storing instructions that, when executed at least one processor, cause the at least one processor to: monitor status of the plurality of physician consoles and the plurality of patient-side robotic procedure systems; receive a first request for status of a physician console or a patient-side robotic procedure system; in response receiving the first request for status, determine an authorization level associated with the first request; in response to determining that the authorization level associated with the first request corresponds to a first authorization level that provides access to status of any physician console or any patient-side robotic procedure system, provide status of the physician console or the patient-side robotic procedure system; in response to determining that the authorization level associated with the first request corresponds to a second authorization level that provides access to status of any physician console of a particular manufacturer type or any patient-side robotic procedure system of the particular manufacturer type: determine a manufacturer type of the physician console or the patient-side robotic procedure system; in response to determining that the manufacturer type of the physician console or the patient-side robotic procedure system matches the particular manufacturer type, provide status of the physician console or the patient-side robotic procedure system; and in response to determining that the manufacturer type of the physician console or the patient-side robotic procedure system does not match the particular manufacturer type, reject provision of status of the physician console or the patient-side robotic procedure system; and in response to determining that the authorization level associated with the first request corresponds to a third authorization level that provides access to status of any physician console or any patient-side robotic procedure system administered by a particular entity: determine an entity administering the physician console or the patient-side robotic procedure system; in response to determining that the entity administering the physician console or the patient-side robotic procedure system matches the particular entity, provide status of the physician console or the patient-side robotic procedure system; and in response to determining that the entity administering the physician console or the patient-side robotic procedure system does not match the particular entity, reject provision of status of the physician console or the patient-side robotic procedure system. The second authorization level and the third authorization level can define a plurality of independent sets of one or more of physician consoles or patient-side robotic procedure systems. A first set associated with the second authorization level can include 1) at least one first physician console or patient-side robotic system that is also included in a second set associated with the third authorization level and 2) at least one second physician console or patent-side robotic system that is not included in the second set.

Clause 2. The system of clause 1, wherein the instructions further cause the at least one processor to: receive a second request to update firmware or software of a physician console or a patient-side robotic procedure system; and in response receiving the second request: determine an authorization level associated with the second request; and in response to determining that the authorization level associated with the second request corresponds to the first or second authorization level, update firmware or software of the physician console or a patient-side robotic procedure system.

Clause 3. The system of clause 2, wherein the instructions further cause the at least one processor to, in response receiving the second request: in response to determining that the authorization level associated with the second request corresponds to the third authorization level, disallow update of firmware or software of the physician console or a patient-side robotic procedure system.

Clause 4. The system of any one of clauses 1 to 3, wherein the instructions further cause the at least one processor to: in response a second request to modify physician access to a physician console or a patient-side robotic procedure system: determine an authorization level associated with the second request; in response to determining that the authorization level associated with the second request corresponds to the first authorization level, modify physician access to the physician console or the patient-side robotic procedure system; and in response to determining that the authorization level associated with the second request corresponds to the third authorization level: determine an entity administering the physician console or the patient-side robotic procedure system; in response to determining that the entity administering the physician console or the patient-side robotic procedure system matches the particular entity, modify physician access to the physician console or the patient-side robotic procedure system; and in response to determining that the entity administering the physician console or the patient-side robotic procedure system does not match the particular entity, not modify physician access to the physician console or the patient-side robotic procedure system.

Clause 5. The system of clause 4, wherein the instructions further cause the at least one processor to: in response to the second request: in response to determining that the authorization level associated with the second request corresponds to the second authorization level, disallow modification of physician access to the physician console or a patient-side robotic procedure system.

Clause 6. The system of any one of clauses 1 to 5, wherein: the first set includes one or more first physician consoles and patient-side robotic procedure systems of a first manufacturer type and a second set includes one or more second physician consoles and patient-side robotic procedure systems of the first manufacturer type; the first set is administered by a first entity; and the second set is administered by a second entity different from the first entity.

Clause 7. The system of any one of clauses 1 to 6, wherein: a set of one or more first physician consoles and patient-side robotic procedure systems administered by a first entity includes physician consoles and patient-side robotic procedure systems of different manufacturer types.

Clause 8. The system of any one of clauses 1 to 7, wherein: the first authorization level allows access to any physician console of the plurality of physician consoles or any patient-side robotic procedure system of the plurality of patient-side robotic procedure systems; the second authorization level allows access to only those physician consoles or those patient-side robotic procedure systems that are manufactured by a particular manufacturer; and the third authorization level allows access to only those physician consoles or those patient-side robotic procedure systems that are administered by a particular healthcare entity.

Clause 9. A method for remotely controlling robotic medical procedures, the method including: by at least one processor: monitoring status of a plurality of physician consoles and a plurality of patient-side robotic procedure systems, wherein: each physician console is configured to: transmit control data to a patient-side robotic procedure system of a plurality of patient-side robotic procedure systems to cause the patient-side robotic procedure system to control one or more of at least one instrument or at least one imaging system, the plurality of physician consoles located remotely from the plurality of patient-side robotic procedure systems; and each robotic procedure system is configured to: receive control data and use the control data to control one or more of at least one instrument or at least one imaging system; and transmit image data obtained by the at least one imaging system to a physician console, wherein the plurality of physician consoles and the plurality of patient-side robotic procedure systems include physician consoles and robotic procedures systems of different manufacturer types and being administered by different entities; receiving a first request for status of a physician console or a patient-side robotic procedure system; responsive receiving the first request for status, determining an authorization level associated with the first request; at a first time: responsive to determining that the authorization level associated with the first request corresponds to a first authorization level that provides access to status of any physician console or any patient-side robotic procedure system, providing status of the physician console or the patient-side robotic procedure system; at a second time: responsive to determining that the authorization level associated with the first request corresponds to a second authorization level that provides access to status of any physician console of a particular manufacturer type or any patient-side robotic procedure system of the particular manufacturer type: determining a manufacturer type of the physician console or the patient-side robotic procedure system; at a third time, responsive to determining that the manufacturer type of the physician console or the patient-side robotic procedure system matches the particular manufacturer type, providing status of the physician console or the patient-side robotic procedure system; and at a fourth time, responsive to determining that the manufacturer type of the physician console or the patient-side robotic procedure system does not match the particular manufacturer type, rejecting provision of status of the physician console or the patient-side robotic procedure system; and at a fifth time: responsive to determining that the authorization level associated with the first request corresponds to a third authorization level that provides access to status of any physician console or any patient-side robotic procedure system administered by a particular entity: determining an entity administering the physician console or the patient-side robotic procedure system; at a sixth time, responsive to determining that the entity administering the physician console or the patient-side robotic procedure system matches the particular entity, providing status of the physician console or the patient-side robotic procedure system; and at a seventh time, responsive to determining that the entity administering the physician console or the patient-side robotic procedure system does not match the particular entity, rejecting provision of status of the physician console or the patient-side robotic procedure system. The second authorization level and the third authorization level can define a plurality of independent sets of one or more of physician consoles or patient-side robotic procedure systems. A first set associated with the second authorization level can include 1) at least one first physician console or patient-side robotic system that is also included in a second set associated with the third authorization level and 2) at least one second physician console or patent-side robotic system that is not included in the second set.

Clause 10. The method of clause 9, further including: receiving a second request to update firmware or software of a physician console or a patient-side robotic procedure system; and responsive receiving the second request: determining an authorization level associated with the second request; and at an eight time, responsive to determining that the authorization level associated with the second request corresponds to the first or second authorization level, updating firmware or software of the physician console or a patient-side robotic procedure system.

Clause 11. The method of clause 10, further including responsive to receiving the second request: at a ninth time: determining that the authorization level associated with the second request corresponds to the third authorization level; and responsive to determining that the authorization level associated with the second request corresponds to the third authorization level, disallowing update of firmware or software of the physician console or a patient-side robotic procedure system.

Clause 12. The method of any one of clauses 9 to 11, further including: responsive to a second request to modify physician access to a physician console or a patient-side robotic procedure system: determining an authorization level associated with the second request; at an eight time, responsive to determining that the authorization level associated with the second request corresponds to the first authorization level, modifying physician access to the physician console or the patient-side robotic procedure system; and at a ninth time, responsive to determining that the authorization level associated with the second request corresponds to the third authorization level: determining an entity administering the physician console or the patient-side robotic procedure system; at a tenth time, responsive to determining that the entity administering the physician console or the patient-side robotic procedure system matches the particular entity, modifying physician access to the physician console or the patient-side robotic procedure system; and at an eleventh time, responsive to determining that the entity administering the physician console or the patient-side robotic procedure system does not match the particular entity, not modifying physician access to the physician console or the patient-side robotic procedure system.

Clause 13. The method of clause 12, further including: responsive to the second request: at a twelfth time, responsive to determining that the authorization level associated with the second request corresponds to the second authorization level, disallowing modification of physician access to the physician console or a patient-side robotic procedure system.

Clause 14. The method of any one of clauses 9 to 13, wherein: the first set includes one or more first physician consoles and patient-side robotic procedure systems of a first manufacturer type and a second set includes one or more second physician consoles and patient-side robotic procedure systems of the first manufacturer type; the first set is administered by a first entity; and the second set is administered by a second entity different from the first entity.

Clause 15. The method of any one of clauses 9 to 14, wherein: a set of one or more first physician consoles and patient-side robotic procedure systems administered by a first entity includes physician consoles and patient-side robotic procedure systems of different manufacturer types.

Clause 16. The method of any one of clauses 9 to 15, wherein: the first authorization level allows access to any physician console of the plurality of physician consoles or any patient-side robotic procedure system of the plurality of patient-side robotic procedure systems; the second authorization level allows access to only those physician consoles or those patient-side robotic procedure systems that are manufactured by a particular manufacturer; and the third authorization level allows access to only those physician consoles or those patient-side robotic procedure systems that are administered by a particular healthcare entity.

Clause 17. A non-transitory computer readable medium storing instructions that, when executed at least one processor, cause the at least one processor to: monitor status of a plurality of physician consoles and a plurality of patient-side robotic procedure systems, wherein: each physician console is configured to: transmit control data to a patient-side robotic procedure system of a plurality of patient-side robotic procedure systems to cause the patient-side robotic procedure system to control one or more of at least one instrument or at least one imaging system, the plurality of physician consoles located remotely from the plurality of patient-side robotic procedure systems; and each robotic procedure system is configured to: receive control data and use the control data to control one or more of at least one instrument or at least one imaging system; and transmit image data obtained by the at least one imaging system to a physician console, wherein the plurality of physician consoles and the plurality of patient-side robotic procedure systems include physician consoles and robotic procedures systems of different manufacturer types and being administered by different entities; receive a first request for status of a physician console or a patient-side robotic procedure system; in response receiving the first request for status, determine an authorization level associated with the first request; in response to determining that the authorization level associated with the first request corresponds to a first authorization level that provides access to status of any physician console or any patient-side robotic procedure system, provide status of the physician console or the patient-side robotic procedure system; in response to determining that the authorization level associated with the first request corresponds to a second authorization level that provides access to status of any physician console of a particular manufacturer type or any patient-side robotic procedure system of the particular manufacturer type: determine a manufacturer type of the physician console or the patient-side robotic procedure system; in response to determining that the manufacturer type of the physician console or the patient-side robotic procedure system matches the particular manufacturer type, provide status of the physician console or the patient-side robotic procedure system; and in response to determining that the manufacturer type of the physician console or the patient-side robotic procedure system does not match the particular manufacturer type, reject provision of status of the physician console or the patient-side robotic procedure system; and in response to determining that the authorization level associated with the first request corresponds to a third authorization level that provides access to status of any physician console or any patient-side robotic procedure system administered by a particular entity: determine an entity administering the physician console or the patient-side robotic procedure system; in response to determining that the entity administering the physician console or the patient-side robotic procedure system matches the particular entity, provide status of the physician console or the patient-side robotic procedure system; and in response to determining that the entity administering the physician console or the patient-side robotic procedure system does not match the particular entity, reject provision of status of the physician console or the patient-side robotic procedure system. The second authorization level and the third authorization level can define a plurality of independent sets of one or more of physician consoles or patient-side robotic procedure systems. A first set associated with the second authorization level can include 1) at least one first physician console or patient-side robotic system that is also included in a second set associated with the third authorization level and 2) at least one second physician console or patent-side robotic system that is not included in the second set.

Clause 18. The non-transitory computer readable medium of clause 17, wherein the instructions further cause the at least one processor to: receive a second request to update firmware or software of a physician console or a patient-side robotic procedure system; and in response to receiving the second request: determine an authorization level associated with the second request; and in response to determining that the authorization level associated with the second request corresponds to the first or second authorization level, update firmware or software of the physician console or a patient-side robotic procedure system.

Clause 19. The non-transitory computer readable medium of clause 18, wherein the instructions further cause the at least one processor to: in response receiving the second request: in response to determining that the authorization level associated with the second request corresponds to the third authorization level, disallow update of firmware or software of the physician console or a patient-side robotic procedure system.

Clause 20. The non-transitory computer readable medium of any one of clauses 17 to 19, wherein the instructions further cause the at least one processor to: in response a second request to modify physician access to a physician console or a patient-side robotic procedure system: determine an authorization level associated with the second request; in response to determining that the authorization level associated with the second request corresponds to the first authorization level, modify physician access to the physician console or the patient-side robotic procedure system; and in response to determining that the authorization level associated with the second request corresponds to the third authorization level: determine an entity administering the physician console or the patient-side robotic procedure system; in response to determining that the entity administering the physician console or the patient-side robotic procedure system matches the particular entity, modify physician access to the physician console or the patient-side robotic procedure system; and in response to determining that the entity administering the physician console or the patient-side robotic procedure system does not match the particular entity, not modify physician access to the physician console or the patient-side robotic procedure system.

Clause 21. The non-transitory computer readable medium of clause 20, wherein the instructions further cause the at least one processor to: in response to receiving the second request: in response to determining that the authorization level associated with the second request corresponds to the second authorization level, disallow modification of physician access to the physician console or a patient-side robotic procedure system.

What is claimed is:

1. A system for remotely controlling robotic medical procedures, the system comprising:

a plurality of physician consoles, each physician console configured to:

transmit control data to a patient-side robotic procedure system of a plurality of patient-side robotic procedure systems to cause the patient-side robotic procedure system to control one or more of at least one instrument or at least one imaging system, the plurality of physician consoles located remotely from the plurality of patient-side robotic procedure systems, the plurality of patient-side robotic procedure systems, each robotic procedure system configured to:

receive control data and use the control data to control one or more of at least one instrument or at least one imaging system; and transmit image data obtained by the at least one imaging system to a physician console, wherein the plurality of physician consoles and the plurality of patient-side robotic procedure systems comprise physician consoles and robotic procedures systems of different manufacturer types and being administered by different entities; and at least one non-transitory computer readable medium storing instructions that, when executed at least one processor, cause the at least one processor to:

monitor status of the plurality of physician consoles and the plurality of patient-side robotic procedure systems;

receive a first request for status of a physician console or a patient-side robotic procedure system;

in response receiving the first request for status, determine an authorization level associated with the first request;

in response to determining that the authorization level associated with the first request corresponds to a first authorization level that provides access to status of any physician console or any patient-side robotic procedure system, provide status of the physician console or the patient-side robotic procedure system;

in response to determining that the authorization level associated with the first request corresponds to a second authorization level that provides access to status of any physician console of a particular manufacturer type or any patient-side robotic procedure system of the particular manufacturer type:

determine a manufacturer type of the physician console or the patient-side robotic procedure system;

in response to determining that the manufacturer type of the physician console or the patient-side robotic procedure system matches the particular manufacturer type, provide status of the physician console or the patient-side robotic procedure system; and in response to determining that the manufacturer type of the physician console or the patient-side robotic procedure system does not match the particular manufacturer type, reject provision of status of the physician console or the patient-side robotic procedure system; and in response to determining that the authorization level associated with the first request corresponds to a third authorization level that provides access to status of any physician console or any patient-side robotic procedure system administered by a particular entity:

determine an entity administering the physician console or the patient-side robotic procedure system;

in response to determining that the entity administering the physician console or the patient-side robotic procedure system matches the particular entity, provide status of the physician console or the patient-side robotic procedure system; and in response to determining that the entity administering the physician console or the patient-side robotic procedure system does not match the particular entity, reject provision of status of the physician console or the patient-side robotic procedure system, wherein the second authorization level and the third authorization level define a plurality of independent sets of one or more of physician consoles or patient-side robotic procedure systems, and wherein a first set associated with the second authorization level includes 1) at least one first physician console or patient-side robotic system that is also included in a second set associated with the third authorization level and 2) at least one second physician console or patent-side robotic system that is not included in the second set.

2. The system of claim 1, wherein the instructions further cause the at least one processor to:

receive a second request to update firmware or software of a physician console or a patient-side robotic procedure system; and in response receiving the second request:

determine an authorization level associated with the second request; and in response to determining that the authorization level associated with the second request corresponds to the first or second authorization level, update firmware or software of the physician console or a patient-side robotic procedure system.

3. The system of claim 2, wherein the instructions further cause the at least one processor to, in response receiving the second request:

in response to determining that the authorization level associated with the second request corresponds to the third authorization level, disallow update of firmware or software of the physician console or a patient-side robotic procedure system.

4. The system of claim 1, wherein the instructions further cause the at least one processor to:

in response a second request to modify physician access to a physician console or a patient-side robotic procedure system:

determine an authorization level associated with the second request;

in response to determining that the authorization level associated with the second request corresponds to the first authorization level, modify physician access to the physician console or the patient-side robotic procedure system; and in response to determining that the authorization level associated with the second request corresponds to the third authorization level:

determine an entity administering the physician console or the patient-side robotic procedure system;

in response to determining that the entity administering the physician console or the patient-side robotic procedure system matches the particular entity, modify physician access to the physician console or the patient-side robotic procedure system; and in response to determining that the entity administering the physician console or the patient-side robotic procedure system does not match the particular entity, not modify physician access to the physician console or the patient-side robotic procedure system.

5. The system of claim 4, wherein the instructions further cause the at least one processor to:

in response to the second request:

in response to determining that the authorization level associated with the second request corresponds to the second authorization level, disallow modification of physician access to the physician console or a patient-side robotic procedure system.

6. The system of claim 1, wherein:

the first set comprises one or more first physician consoles and patient-side robotic procedure systems of a first manufacturer type and a second set comprises one or more second physician consoles and patient-side robotic procedure systems of the first manufacturer type;

the first set is administered by a first entity; and the second set is administered by a second entity different from the first entity.

7. The system of claim 1, wherein:

a set of one or more first physician consoles and patient-side robotic procedure systems administered by a first entity comprises physician consoles and patient-side robotic procedure systems of different manufacturer types.

8. The system of claim 1, wherein:

the first authorization level allows access to any physician console of the plurality of physician consoles or any patient-side robotic procedure system of the plurality of patient-side robotic procedure systems;

the second authorization level allows access to only those physician consoles or those patient-side robotic procedure systems that are manufactured by a particular manufacturer; and the third authorization level allows access to only those physician consoles or those patient-side robotic procedure systems that are administered by a particular healthcare entity.

9. A method for remotely controlling robotic medical procedures, the method comprising:

by at least one processor:

monitoring status of a plurality of physician consoles and a plurality of patient-side robotic procedure systems, wherein:

each physician console is configured to:

transmit control data to a patient-side robotic procedure system of a plurality of patient-side robotic procedure systems to cause the patient-side robotic procedure system to control one or more of at least one instrument or at least one imaging system, the plurality of physician consoles located remotely from the plurality of patient-side robotic procedure systems; and each robotic procedure system is configured to:

receive control data and use the control data to control one or more of at least one instrument or at least one imaging system; and transmit image data obtained by the at least one imaging system to a physician console, wherein the plurality of physician consoles and the plurality of patient-side robotic procedure systems comprise physician consoles and robotic procedures systems of different manufacturer types and being administered by different entities;

receiving a first request for status of a physician console or a patient-side robotic procedure system;

responsive receiving the first request for status, determining an authorization level associated with the first request;

at a first time:

responsive to determining that the authorization level associated with the first request corresponds to a first authorization level that provides access to status of any physician console or any patient-side robotic procedure system, providing status of the physician console or the patient-side robotic procedure system;

at a second time:

responsive to determining that the authorization level associated with the first request corresponds to a second authorization level that provides access to status of any physician console of a particular manufacturer type or any patient-side robotic procedure system of the particular manufacturer type:

determining a manufacturer type of the physician console or the patient-side robotic procedure system;

at a third time, responsive to determining that the manufacturer type of the physician console or the patient-side robotic procedure system matches the particular manufacturer type, providing status of the physician console or the patient-side robotic procedure system; and at a fourth time, responsive to determining that the manufacturer type of the physician console or the patient-side robotic procedure system does not match the particular manufacturer type, rejecting provision of status of the physician console or the patient-side robotic procedure system; and at a fifth time:

responsive to determining that the authorization level associated with the first request corresponds to a third authorization level that provides access to status of any physician console or any patient-side robotic procedure system administered by a particular entity:

determining an entity administering the physician console or the patient-side robotic procedure system;

at a sixth time, responsive to determining that the entity administering the physician console or the patient-side robotic procedure system matches the particular entity, providing status of the physician console or the patient-side robotic procedure system; and at a seventh time, responsive to determining that the entity administering the physician console or the patient-side robotic procedure system does not match the particular entity, rejecting provision of status of the physician console or the patient-side robotic procedure system, wherein the second authorization level and the third authorization level define a plurality of independent sets of one or more of physician consoles or patient-side robotic procedure systems, and wherein a first set associated with the second authorization level includes 1) at least one first physician console or patient-side robotic system that is also included in a second set associated with the third authorization level and 2) at least one second physician console or patent-side robotic system that is not included in the second set.

10. The method of claim 9, further comprising:

receiving a second request to update firmware or software of a physician console or a patient-side robotic procedure system; and responsive receiving the second request:

determining an authorization level associated with the second request; and at an eight time, responsive to determining that the authorization level associated with the second request corresponds to the first or second authorization level, updating firmware or software of the physician console or a patient-side robotic procedure system.

11. The method of claim 10, further comprising responsive to receiving the second request:

at a ninth time:

determining that the authorization level associated with the second request corresponds to the third authorization level; and responsive to determining that the authorization level associated with the second request corresponds to the third authorization level, disallowing update of firmware or software of the physician console or a patient-side robotic procedure system.

12. The method of claim 9, further comprising:

responsive to a second request to modify physician access to a physician console or a patient-side robotic procedure system:

determining an authorization level associated with the second request;

at an eight time, responsive to determining that the authorization level associated with the second request corresponds to the first authorization level, modifying physician access to the physician console or the patient-side robotic procedure system; and at a ninth time, responsive to determining that the authorization level associated with the second request corresponds to the third authorization level:

determining an entity administering the physician console or the patient-side robotic procedure system;

at a tenth time, responsive to determining that the entity administering the physician console or the patient-side robotic procedure system matches the particular entity, modifying physician access to the physician console or the patient-side robotic procedure system; and at an eleventh time, responsive to determining that the entity administering the physician console or the patient-side robotic procedure system does not match the particular entity, not modifying physician access to the physician console or the patient-side robotic procedure system.

13. The method of claim 12, further comprising:

responsive to the second request:

at a twelfth time, responsive to determining that the authorization level associated with the second request corresponds to the second authorization level, disallowing modification of physician access to the physician console or a patient-side robotic procedure system.

14. The method of claim 9, wherein:

the first set comprises one or more first physician consoles and patient-side robotic procedure systems of a first manufacturer type and a second set comprises one or more second physician consoles and patient-side robotic procedure systems of the first manufacturer type;

the first set is administered by a first entity; and the second set is administered by a second entity different from the first entity.

15. The method of claim 9, wherein:

a set of one or more first physician consoles and patient-side robotic procedure systems administered by a first entity comprises physician consoles and patient-side robotic procedure systems of different manufacturer types.

16. The method of claim 9, wherein:

the first authorization level allows access to any physician console of the plurality of physician consoles or any patient-side robotic procedure system of the plurality of patient-side robotic procedure systems;

the second authorization level allows access to only those physician consoles or those patient-side robotic procedure systems that are manufactured by a particular manufacturer; and the third authorization level allows access to only those physician consoles or those patient-side robotic procedure systems that are administered by a particular healthcare entity.

17. A non-transitory computer readable medium storing instructions that, when executed at least one processor, cause the at least one processor to:

monitor status of a plurality of physician consoles and a plurality of patient-side robotic procedure systems, wherein:

each physician console is configured to:

transmit control data to a patient-side robotic procedure system of a plurality of patient-side robotic procedure systems to cause the patient-side robotic procedure system to control one or more of at least one instrument or at least one imaging system, the plurality of physician consoles located remotely from the plurality of patient-side robotic procedure systems; and each robotic procedure system is configured to:

receive control data and use the control data to control one or more of at least one instrument or at least one imaging system; and transmit image data obtained by the at least one imaging system to a physician console, wherein the plurality of physician consoles and the plurality of patient-side robotic procedure systems comprise physician consoles and robotic procedures systems of different manufacturer types and being administered by different entities;

receive a first request for status of a physician console or a patient-side robotic procedure system;

in response receiving the first request for status, determine an authorization level associated with the first request;

in response to determining that the authorization level associated with the first request corresponds to a first authorization level that provides access to status of any physician console or any patient-side robotic procedure system, provide status of the physician console or the patient-side robotic procedure system;

in response to determining that the authorization level associated with the first request corresponds to a second authorization level that provides access to status of any physician console of a particular manufacturer type or any patient-side robotic procedure system of the particular manufacturer type:

determine a manufacturer type of the physician console or the patient-side robotic procedure system;

in response to determining that the manufacturer type of the physician console or the patient-side robotic procedure system matches the particular manufacturer type, provide status of the physician console or the patient-side robotic procedure system; and in response to determining that the manufacturer type of the physician console or the patient-side robotic procedure system does not match the particular manufacturer type, reject provision of status of the physician console or the patient-side robotic procedure system; and in response to determining that the authorization level associated with the first request corresponds to a third authorization level that provides access to status of any physician console or any patient-side robotic procedure system administered by a particular entity:

determine an entity administering the physician console or the patient-side robotic procedure system;

in response to determining that the entity administering the physician console or the patient-side robotic procedure system matches the particular entity, provide status of the physician console or the patient-side robotic procedure system; and in response to determining that the entity administering the physician console or the patient-side robotic procedure system does not match the particular entity, reject provision of status of the physician console or the patient-side robotic procedure system, wherein the second authorization level and the third authorization level define a plurality of independent sets of one or more of physician consoles or patient-side robotic procedure systems, and wherein a first set associated with the second authorization level includes 1) at least one first physician console or patient-side robotic system that is also included in a second set associated with the third authorization level and 2) at least one second physician console or patent-side robotic system that is not included in the second set.

18. The non-transitory computer readable medium of claim 17, wherein the instructions further cause the at least one processor to:

receive a second request to update firmware or software of a physician console or a patient-side robotic procedure system; and in response to receiving the second request:

determine an authorization level associated with the second request; and in response to determining that the authorization level associated with the second request corresponds to the first or second authorization level, update firmware or software of the physician console or a patient-side robotic procedure system.

19. The non-transitory computer readable medium of claim 18, wherein the instructions further cause the at least one processor to:

in response receiving the second request:

in response to determining that the authorization level associated with the second request corresponds to the third authorization level, disallow update of firmware or software of the physician console or a patient-side robotic procedure system.

20. The non-transitory computer readable medium of claim 17, wherein the instructions further cause the at least one processor to:

in response a second request to modify physician access to a physician console or a patient-side robotic procedure system:

determine an authorization level associated with the second request;

in response to determining that the authorization level associated with the second request corresponds to the first authorization level, modify physician access to the physician console or the patient-side robotic procedure system; and in response to determining that the authorization level associated with the second request corresponds to the third authorization level:

determine an entity administering the physician console or the patient-side robotic procedure system;

in response to determining that the entity administering the physician console or the patient-side robotic procedure system matches the particular entity, modify physician access to the physician console or the patient-side robotic procedure system; and in response to determining that the entity administering the physician console or the patient-side robotic procedure system does not match the particular entity, not modify physician access to the physician console or the patient-side robotic procedure system.

21. The non-transitory computer readable medium of claim 20, wherein the instructions further cause the at least one processor to:

in response to receiving the second request:

in response to determining that the authorization level associated with the second request corresponds to the second authorization level, disallow modification of physician access to the physician console or a patient-side robotic procedure system.

* * * * *